United States Patent
Castro et al.

(10) Patent No.: US 8,741,578 B2
(45) Date of Patent: Jun. 3, 2014

(54) METHODS OF DETECTING CHRONIC LYMPHOCYTIC LEUKEMIA WITH HSP90 AND ZAP-70

(75) Inventors: Januario E. Castro, San Diego, CA (US); Thomas J. Kipps, Rancho Santa Fe, CA (US); Carlos E. Prada, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 1028 days.

(21) Appl. No.: 11/666,899

(22) PCT Filed: Nov. 1, 2005

(86) PCT No.: PCT/US2005/039406
§ 371 (c)(1),
(2), (4) Date: Oct. 4, 2007

(87) PCT Pub. No.: WO2006/050333
PCT Pub. Date: May 11, 2006

(65) Prior Publication Data
US 2008/0193928 A1 Aug. 14, 2008

Related U.S. Application Data

(60) Provisional application No. 60/624,638, filed on Nov. 2, 2004, provisional application No. 60/624,660, filed on Nov. 2, 2004.

(51) Int. Cl.
*G01N 33/53* (2006.01)
*G01N 33/574* (2006.01)

(52) U.S. Cl.
CPC .... *G01N 33/57426* (2013.01); *G01N 33/57484* (2013.01); *G01N 33/53* (2013.01)
USPC ........................... 435/7.1; 435/7.21; 435/7.23

(58) Field of Classification Search
CPC ............ G01N 33/53; G01N 33/57426; G01N 33/57484
See application file for complete search history.

(56) References Cited

U.S. PATENT DOCUMENTS

| | | | |
|---|---|---|---|
| 2003/0105000 A1* | 6/2003 | Pero et al. ........................ | 514/12 |
| 2003/0114450 A1 | 6/2003 | Santi et al. | |
| 2003/0194409 A1 | 10/2003 | Rothman et al. | |
| 2005/0119282 A1 | 6/2005 | Kasibhatla et al. | |

FOREIGN PATENT DOCUMENTS

WO    WO 2006/050457 A2    5/2006

OTHER PUBLICATIONS

Cotterchio et al, 2000, Chronic Diseases in Canada, (Electronic Version downloaded from www.phac-aspc.gc.ca/publicat/cdic-mcc/21-2/f_e.html).*
Martin et al (Journal of the National Cancer Institute, 2000, 92:1126-1135).*
Taber's Cyclopedic Medical Dictionary (1985, F.A. Davis Company, Philadelphia, p. 274).*
Busken, C et al. (Digestive Disease Week Abstracts and Itinerary Planner, 2003, abstract No:850).*
Kaiser (Science, 2006, 313: 1370).*
Boyd (The Basic Science of Oncology, 1992, McGraw-Hill, Inc., p. 379).*
Rosenwald et al. (J. Exp. Medicine Dec. 2001 194:1639-1647).*
Tockman et al (Cancer Res., 1992, 52:2711s-2718s).*
Bowie et al (Science, 1990, 257:1306-1310).*
Rudikoff et al, (PNAS, USA, 1982, 79: 1979-1983).*
Burgess et al ( J of Cell Bio. 111:2129-2138, 1990).*
Lazar et al (Molecular and Cellular Biology, 1988, 8:1247-1252).*
Benedict et al (J. Exp. Medicine, 2001, 193(1) 89-99).*
Jiang et al (JBC, 2003, 278(7) 4763-4769).*
Matsushita et al (FEBS Letters, 1999, vol. 443, pp. 348-352) teaches.*
Singh et al (Glycobiology, 2001, vol. 11, pp. 587-592).*
Prada et al. (Blood, Nov. 16, 2004, vol. 104, No. 11, part 1, pp. 767A).*
Hornbeck et al. (Current Protocols in Mol. Biol. Enzyme-Linked Immunosorbent Assays (ELISA) 2000, 11.2.1-11.2.22).*
Jones et al. (Blood, Oct. 23, 2003 103(5): 1855-1861).*
Castro, Januario E., Carlos E. Prada, Olivier Loria, Adeela Kamal, Liguang Chen, Francis J. Burrows and Thomas J. Kipps, "ZAP-70 is a novel conditional heat shock protein 90 (Hsp90) client: inhibition of Hsp90 leads to ZAP-70 degradation, apoptosis, and impaired signaling in chronic lymphocytic leukemia" Blood, Oct. 1, 2005, vol. 106, No. 7, pp. 2506-2512.
Wiestner, Adrian, "More ZAP for chronic lymphocytic leukemia (CLL)", Blood, Mar. 1, 2005, vol. 105, No. 5, pp. 1839-1840.
Jones, Dylan T., Elena Addison, Janet M. North, Mark W. Lowdell, A. Victor Hoffbrand, Atul B. Mehta, Kanagasabai Ganeshaguru, Najeem I. Folarin and R. Gitendra Wickremasinghe, "Geldanamycin and herbimycin A induce apoptotic killing of B chronic lymphocytic leukemia cells and augment the cells sensitivity to cytotoxic drugs" Blood, Mar. 1, 2004, vol. 103, vol. 5, pp. 1855-1861.
Matsuda, Satoshi, Tomoko Suzuki-Fujimoto, Akiko Minowa, Hideki Ueno, Kenji Katamura and Shigeo Koyasu "Temperature-sensitive ZAP70 Mutants Degrading through a Proteasome-independent Pathway" The Journal of Biological Chemistry, Dec. 3, 1999, vol. 274, No. 49, pp. 34515-34518.
Durig, J., H. Nuckel, M. Cremer, A. Fuhrer, K. Halfmeyer, J. Fandrey, T. Moroy, L. Klein-Hitpass and U. Duhrsen "ZAP-70 expression is a prognostic factor in chronic lymphocytic leukemia" Leukemia, Oct. 2, 2003, 17, pp. 2426-2434.

* cited by examiner

*Primary Examiner* — Peter J Reddig
(74) *Attorney, Agent, or Firm* — Joseph R. Baker, Jr.; Gavrilovich, Dodd & Lindsey LLP

(57) ABSTRACT

Provided are compositions and methods useful for treating and diagnosing cell proliferative disorders associated with Hsp90 and/or ZAP-70.

15 Claims, 7 Drawing Sheets

METHODS OF DETECTING CHRONIC LYMPHOCYTIC LEUKEMIA WITH HSP90 AND ZAP-70

CROSS REFERENCE TO RELATED APPLICATIONS

This application is filed under 35 U.S.C. §371 and claims priority to International Application Serial No. PCT/US2005/ 0039406, filed Nov. 1, 2005, which claims priority under 35 U.S.C. §119 to Provisional Application Ser. No. 60/624,660, filed Nov. 2, 2004, and U.S. Provisional Application Ser. No. 60/624,638. filed Nov. 2, 2004, the disclosures of which are incorporated herein by reference.

TECHNICAL FIELD

This invention relates to methods and compositions for modulating apoptosis by selective inhibition of heat shock proteins. More particularly the invention is directed to methods and composition for inducing apoptosis of cancer cells.

BACKGROUND

There exists a need in the art to identify key interactions between proteins involved in the apoptotic pathway and to regulate those interactions to treat various diseases and disorders.

The progress of CLL varies. In aggressive CLL, cells express an unmutated immunoglobulin (Ig) heavy-chain variable region ($V_H$) and ZAP-70. In contrast indolent CLL cells express a mutated $IgV_H$ but lack ZAP-70 expression.

SUMMARY

The invention provides the first evidence that an Hsp90 plays an active role in CLL. Furthermore, the invention provides that Hsp90 inhibitors induce apoptosis in CLL cells. Furthermore, the invention provides for the first time the ability to induce apoptosis by downregulating ZAP-70. Furthermore, the invention provides for the first time the ability to use Hsp90 complexes as a prognostic marker in cancer.

The invention provides a method of determining the prognosis or diagnosis of a subject at risk for a cell proliferative disorder comprising determining the presence of (i) an Hsp90-ZAP-70 complex and/or (ii) determining an amount of activated Hsp90 in a cell that expresses ZAP-70.

The invention also provides a method of detecting chronic lymphocytic leukemia (CLL) in a subject, comprising determining (i) an Hsp90-ZAP-70 complex and/or (ii) an amount of activated Hsp90 in a cell that expresses ZAP-70, wherein if (i) and/or (ii) is elevated compared to a control the amount is indicative chronic lymphocytic leukemia in the subject. In a particular embodiment, the complex can be detected by immunocytochemistry. In another embodiment, the complex can be detected by relative mobility (Mr) shift in a gel. In a further embodiment the method of detecting chronic lymphocytic leukemia (CLL) in a subject, further comprises determining the expression of one or more additional polynucleotides or polypeptides associated with CLL. In yet a further embodiment, the one or more additional polynucleotides or polypeptides is selected from the group consisting of a nucleic acid encoding IM1286077, an IM1286077 polypeptide, a nucleic acid encoding activation-induced C-type lectin, and an activation-induced C-type lectin.

The invention further provides a method of determining the prognosis or diagnosis of a subject at risk for a cell proliferative disorder comprising determining the presence of activated Hsp90 in the subject. In one aspect, the method further comprises determining the level of ZAP-70.

The invention provides a method of modulating apoptosis in a cell, the method comprising contacting an Hsp90 and/or ZAP-70 polypeptide with an agent that (i) inhibits Hsp90 and/or ZAP-70 activity, (ii) inhibits or prevents the ability of Hsp90 and ZAP-70 to interact and/or (iii) inhibits the production of Hsp90 and/or ZAP-70. The cell may be contacted in vitro or in vivo.

The invention further provides a method of treating leukemia in a subject, the method comprising contacting a subject with an agent that (i) inhibits Hsp90 and/or ZAP-70 activity, (ii) inhibits or prevents the ability of Hsp90 and ZAP-70 to interact and/or (iii) inhibits the production of Hsp90 and/or ZAP-70.

Also provided by the invention is a kit comprising reagents useful for detecting (i) Hsp90 and ZAP-70 and/or (ii) an Hsp90-ZAP-70 complex in a sample.

The details of one or more embodiments are set forth in the accompanying drawings and the description below. Other features, objects, and advantages will be apparent from the description and drawings, and from the claims.

DETAILED DESCRIPTION

Figure 1:
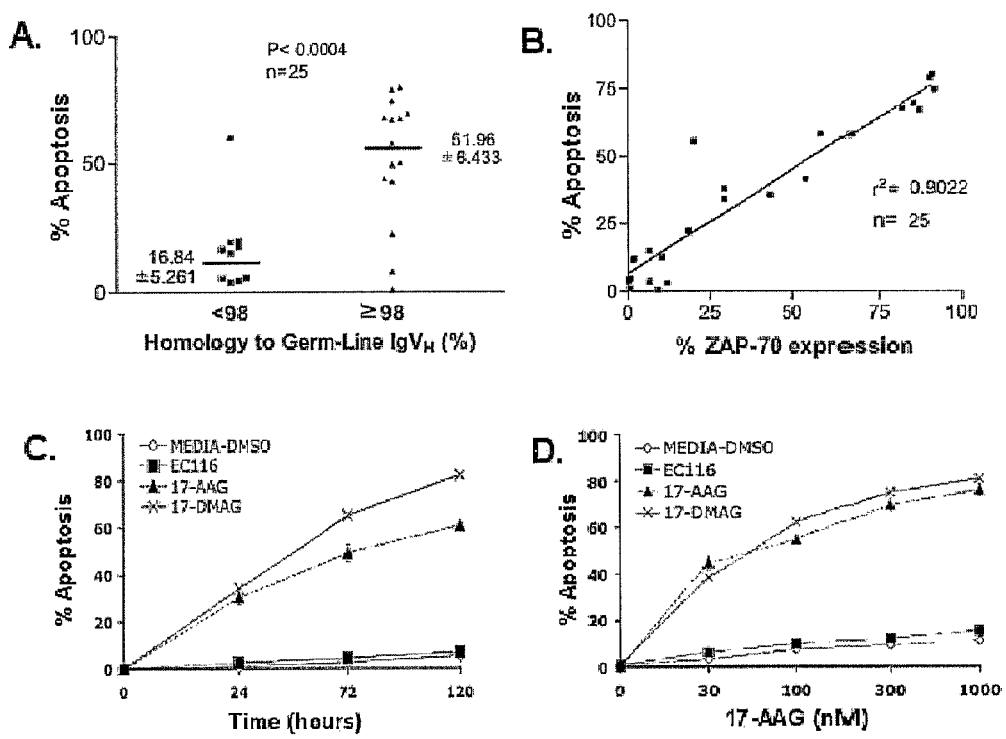
FIGS. 1A-D shows that Hsp90 inhibitors induce apoptosis in CLL cells that express adverse prognostic markers. (A) Cell apoptosis was measured in CLL cells (n=25), after in vitro treatment with 17-AAG at 100 nM during 48 hours. $IgV_H$ gene mutation was assessed by gene sequencing. Sequences with less than 98 percent homology to the corresponding germ-line $IgV_H$ sequence were considered mutated. (B) Correlation by linear regression of the level of expression of ZAP-70 and apoptosis induced by 17-AAG (100 nM) after 48 hours of incubation in CLL samples. (C and D) Cell death was assessed in ZAP-70$^+$ CLL cells after treatment with 17-AAG, 17-DMAG and EC116 using 100 nM at different time points and also during 48 hours using increasing concentrations.

As used herein and in the appended claims, the singular forms "a," "and," and "the" include plural referents unless the context clearly dictates otherwise. Thus, for example, reference to "a cell" includes a plurality of such cells and reference to "the polypeptide" includes reference to one or more polypeptides known to those skilled in the art, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed herein are provided solely for their disclosure prior to the filing date of the present application. Nothing herein is to be construed as an admission that the inventors are not entitled to antedate such disclosure by virtue of prior disclosure.

The Hsp90 family of proteins is a group of highly conserved stress proteins that are expressed in eukaryotic cells, and are essential in yeast and Drosophila. For a general review of heat shock proteins, see Parsell and Lindquist, 1993, Ann. Rev. Genet. 27:437-496, incorporated herein by reference. Hsp90 is one of the most abundant proteins in the eukaryotic cell, constituting up to about 1-2% of the cellular protein under normal physiologic conditions, and its expression is increased several-fold in response to stress. Although family members of Hsp90 have interchangeable functions, the respective genes are differentially regulated in eukaryotes. Borkovich et al., 1989, Mol. Cell Biol. 9:3919-3930. In most eukaryotic cells, one of two Hsp90 family members is expressed constitutively at a high level at physiological temperature and is induced 2-3 fold by heat shock. A second family member is expressed at a low basal level at normal temperatures, but its expression is enhanced strongly under restrictive growth conditions, like heat treatment. See, Borkovich et al., supra; Krone and Sass, 1994, Biochem. Biophys. Res. Commun. 204:746-752.

The two genes that encode Hsp90 in humans, Hsp90-α and Hsp90-β, are 86% homologous. Further, there is extensive homology with lower species. The 63 kDa Hsp90 homolog in Escherichia coli is 42% identical in amino acid sequence to human Hsp90. The 83 kDa Hsp90 protein homolog of Drosophila (Hsp83) is 78% identical to human Hsp90. See, e.g., Alique et al., 1994, EMBO J. 13:6099-6106; Rebbe et al., 1987, Gene 53:235-245; Blackman et al., 1986, J. Mol. Biol. 188:499-515, all of which are incorporated herein by reference.

The Hsp90 family has been implicated as an important component of intracellular signaling pathways as well as in assisting protein folding. Dimeric Hsp90 proteins bind molecules such as steroid hormone receptors and the receptor kinases v-src, Raf, and casein kinase II (Catelli et al., 1985, EMBO J. 4:3131-3135; Miyata and Yahara, 1992, J. Biol. Chem. 267:7042-7047; Stancato et al., 1993, J. Biol. Chem. 268:21711-21716; Xu and Lindquist, 1993, Proc. Natl. Acad. Sci, USA 90:7074-7078; Wartmann and Davis, 1994, J. Biol. Chem. 269:6695-6701; van der Straten et al., 1997, EMBO J. 16:1961-1969). In the case of steroid receptors, this interaction is required for efficient ligand binding and transcriptional regulation (Bohen and Yamamoto, 1994, Modulation of Steroid Receptor Signal Transduction by Heat Shock Proteins, In: The Biology of Heat Shock Proteins and Molecular Chaperones, Cold Spring Harbor Laboratory Press, pp. 313-334).

In order to exert its function on client proteins, Hsp90 forms an active protein complex comprising the cochaperone molecule and an active ATP binding site. Proteins that have been identified as Hsp90 client proteins include transmembrane tyrosine kinases (Her-2/neu, epidermal growth factor receptor (EGFR), MET and insulin-like growth factor-1 receptor (IGF-1R), metastable signaling proteins (Akt, Raf-1 and IKK), mutated signaling proteins (p53, Kit, Flt3 and v-src), chimeric signaling proteins (NPM-ALK, Bcr-Abl), steroid receptors (androgen, estrogen and progesterone receptors), cell-cycle regulators (cdk4, cdk6) and apoptosis related proteins.

Zeta-associated protein (ZAP) 70 is a 70 KDa protein tyrosine kinase that is expressed in T cells and NK cells. ZAP-70 is known to play a role in T cell activation. Genetic alterations in the ZAP-70 gene that cause loss of expression of ZAP-70 in humans prevent antigen activation of $CD4^+$ T cells, inhibit maturation of $CD8^+$ T cells, and lead to severe combined immunodeficiencies.

The first 259 residues of ZAP-70 consist of two SH2 domains that are connected by a 65 residue segment and are followed by a second connecting region and a catalytic domain. SH2 domains consist of approximately 100 amino acids. Their role in the specific recognition of tyrosine-phosphorylated proteins is integral to a variety of intracellular signaling events. Several SH2 domains have been demonstrated to retain the ability to bind with high affinity to short peptides that contain phosphotyrosine (pY) when expressed as isolated proteins. Selectivity for isolated SH2 domains is dependent upon recognition of residues immediately C-terminal to the phosphorylated tyrosine (pY+n). In order to bind to the TCR, ZAP requires that both of its SH2 domains are present and functional and that both tyrosines within the ITAM are phosphorylated.

ZAP-70 has been shown to be expressed in patients with aggressive chronic lymphocytic leukemia (CLL). The invention demonstrates that $ZAP-70^+$ CLL cells, expressed activated heat-shock protein 90 (Hsp90) with high binding-affinity for Hsp90-inhibitors, such as 17-allyl-aminodemethoxygeldanamycin (17-AAG), whereas normal lymphocytes or ZAP-70-negative CLL cells express non-activated Hsp90.

The invention further demonstrates that activated Hsp90 interacts with and stabilizes ZAP-70, which behaves like an Hsp90 client protein in CLL cells. Treatment with agents that disrupted Hsp90 activity, induced ZAP-70 degradation and apoptosis in CLL cells but not in T cells, and also impaired B-cell receptor signaling in leukemia cells.

The invention demonstrates that Hsp90 facilitates ZAP-70 expression and activity; that ZAP-70 is unique among Hsp90 clients, in that its chaperone-dependency is conditional upon the cell type in which it is expressed, and also that ZAP-70 promotes cell survival and signaling in CLL. Additionally, ZAP-70 expression in CLL cells confers markedly heightened sensitivity to, for example, 17-AAG or 17-DMAG, demonstrating that these and other Hsp90 inhibitors (as described more fully herein) are valuable therapeutics in patients with CLL.

The invention provides for the first time an association of ZAP-70 and Hsp90. Furthermore, this association has been linked to cell proliferative disorders. For example, the invention demonstrates that ZAP-70 is an Hsp90 client protein. ZAP-70 expression is indicative of chronic lymphocytic leukemla (CLL) and small lymphocytic lymphoma (SLL). Thus, in one aspect, the invention provides a method of diagnosing a cell proliferative disorder (e.g., CLL and/or SLL), by determining the presence and/or amount of Hsp90-ZAP-70 complex in a biological sample. In another aspect, the invention prove des a method of diagnosing a cell proliferative disorder (e.g., CLL and/or SLL) by measuring the presence of activated Hsp90 and ZAP-70.

In another aspect, the invention provides methods and compositions for diagnosing a cell proliferative disorder while reducing false positives by setting a threshold ZAP-70 determination.

The invention also provides methods and compositions useful to screen for apoptotic agents (e.g., agents useful to treat leukemia) by identifying agents that disrupt an Hsp90-ZAP-70 complex or formation of such a complex.

Many methods are known in the art for determining protein concentrations and measuring or predicting the level of proteins within cells and in fluid samples. Indirect techniques include nucleic acid hybridization and amplification using, for example, polymerase chain reaction (PCR). These techniques are known to the person of skill and are discussed in, for example, Sambrook, Fritsch & Maniatis, Molecular Cloning: A Laboratory Manual, Second Edition (1989) Cold Spring Harbor Laboratory Press, Cold Spring Harbor, N.Y., Ausubel, et al., Current Protocols IN Molecular Biology, John Wiley & Sons, N.Y., 1994.

U.S. patent application Ser. No. 10/309,548 describes various methods for diagnosing CLL and SLL by measuring ZAP-70 expression and unmutated $IgV_H$. However, in one study 23 percent of the patients studied had CLL cells that expressed mutated $IgV_H$ and ZAP-70 or expressed unmutated $IgV_H$ but lacked expression of ZAP-70. Thus, although ZAP-70 has been associated with CLL, the mere presence of ZAP-70 can lead to false negatives.

The invention demonstrates that Hsp90 chaperoning of ZAP-70 is limited to CLL cells and is not observed in T cells where this kinase is normally expressed. In particular ZAP-70 is unique among identified Hsp90 clients as its chaperone dependency is conditional upon the type of cell in which it is expressed. Accordingly, the measurement of Hsp90-ZAP-70 complex is indicative of CLL cells in subject.

In addition, the invention provides a method of identifying a pharmacologic active dose for a subject by determining the down-modulation of ZAP-70. In one aspect, the dose is the dose of an Hsp90 inhibitor. It is possible that such Hsp90 inhibitors may have activity in patients who have leukemia cells that lack ZAP-70 expression owing to the down-modulation of other proteins. Finding the optimal dose of an Hsp90 inhibitor will be facilitated by monitoring the levels of ZAP-70 in leukemia cells treated with such inhibitors. As such, this allows for defining a surrogate endpoint of a biologic response, which could be defined at certain plasma/serum concentrations and/or dosing regimens. Such a method is useful in determining an optimal method to administer Hsp90 inhibitors in patients with CLL or cancer in general.

In determining the diagnosis or prognosis of a subject suspected of having or having a cell proliferative disorder such as CLL or SLL, a sample will be obtained from the subject. For the purposes of determining an Hsp90-ZAP-70 complex, a biological sample of the subject is used, which sample includes cellular proteins. Such a biological sample may be obtained from body cells, such as those present in peripheral blood, urine, saliva, tissue biopsy, amniocentesis samples, surgical specimens and autopsy material. Biological samples can be obtained from normal, healthy subjects or from subjects who are predisposed to or who are suffering from a leukemia such as, but not limited to, CLL.

For example, whole blood cells from patients with CLL or suspected of having CLL can be obtained. The whole blood cells are treated with 17-AAG at different concentrations at room temperature. Red cells are lysed using ammonium-chloride buffer. The cells are stained with specific antibodies and DiOC6. Samples are analyzed by flow cytometry to show a density plot of cells labeled with anti-CD5 and anti-CD19. Cell death was assessed in the CLL subpopulation and the panel shows the percentage of CLL apoptotic cells based in the MFI value for DiOC6. These experiments were performed and reproduced several times. This technique allows for a rapid method of determining CLL as well as determining the responsiveness of CLL in subject with CLL. The method can be performed simply and rapidly and does not require cell isolation or purification, but rather relies on direct blood draw. The induction by 17-AAG of apoptosis is exclusively in the ZAP-70 positive cells. These data demonstrate that the test can be used for detection of high risk patients and potentially can be automated and used for high throughput screening. For example, kits comprising 17-AAG, lysis buffer, DiOC6, and/or anti-CD5 and anti-CD19 antibodies can be prepared for rapid detection by flow cytometric methods and described above.

In one aspect of the invention, a blood sample is collected from a subject. The sample is then treated with an Hsp-90 inhibitor (e.g., 17AAG) and then the number of lymphocytic leukemia cells measured by flow cytometry using anti-CD5 and/or anti-CD19. The sample may be split before incubation to generate a control that is not treated with the Hsp90 inhibitor to determine the amount of apoptosis within a sample from a subject. Alternatively, the amount of apoptosis may be compared to a known standard sample.

Several other methods are available for the quantification of protein-protein interactions (e.g., Hsp90-ZAP-70 complexes) in the sample. For example, fluorescence polarization techniques are suitable for the measurement of binding events. Available cell-based methods involve fluorescent or bioluminescent assays of protein-protein interactions, and include resonance energy transfer (FRET or BRET), enzyme subunit complementation, and protein-fragment complementation assays (PCA). It will be understood by one skilled in the art that the invention is not limited to the exact assay methodology that is selected, to the detection method, or to particular instrumentation.

One of the most widespread fluorescent, cell-based protein-protein interaction assays is based on the phenomenon of fluorescence resonance energy transfer (FRET) or bioluminescence resonance energy transfer (BRET). In a FRET assay the genes for two different fluorescent reporters, capable of undergoing FRET are separately fused to genes encoding a polypeptide of interest (e.g., Hsp90 and ZAP-70), and the fusion proteins are co-expressed in live cells. When a protein complex forms between the proteins of interest, the fluorophores are brought into proximity if the two proteins possess overlapping emission and excitation, emission of photons by a first, "donor" fluorophore, results in the efficient absorption of the emitted photons by the second, "acceptor" fluoxophore. The FRET pair fluoresces with a unique combination of excitation and emission wavelengths that can be distinguished from those of either fluorophore alone in living cells. As specific examples, a variety of GFP mutants have been used in FRET assays, including cyan, citrine, enhanced green and enhanced blue fluorescent proteins. With BRET, a luminescent protein—for example the enzyme Renilla luciferase (RLuc)—is used as a donor and a green fluorescent protein (GFP) is used as an acceptor molecule. Upon addition of a compound that serves as the substrate for Rluc, the FRET signal is measured by comparing the amount of blue light emitted by Rluc to the amount of green light emitted by GFP. The ratio of green to blue increases as the two proteins are brought into proximity associates with quantifying simple FRET intensity. The same principle can work with respect to labeling Hsp90 and ZAP-70 polypeptides using small molecules, antibodies, peptides and the like.

Another method of discriminating between clinical subgroups of CLL/SLL is to examine, and in some instances quantitate (either comparatively or in absolute terms), the level of Hsp90-ZAP-70 complex or the ratio of activated Hsp90 and ZAP-70 in the cells of a subject. For example, in one aspect, an amount of ZAP-70 polynucleotide or polypeptide in a sample that is more the 20% greater than a control is indicative of leukemia. The term ZAP-70 positive" and ZAP-70 negative" are based on a cutoff expression of 20% as measured by flow cytometry.

The availability of antibodies specific to the Hsp90 protein, ZAP-70 protein and/or Hsp90-ZAP-70 protein complexes facilitates the examination of such proteins and complexes by one of a number of immunoassay methods, which are known in the art and are presented herein and in, for instance, Harlow and Lane (Antibodies, A Laboratory Manual, CSHL, New York, 1988).

Antibodies can be used to assess the presence or absence of ZAP-70 in cultured cells or primary cells. The determination that an antibody specifically detects an Hsp90, ZAP-70, and/or protein complex is made by any one of a number of standard immunoassay methods; for instance, the Western blotting technique (Sambrook et al., In Molecular Cloning: A Laboratory Manual, CSHL, New York, 1989).

In one specific, non-limiting embodiment total cellular protein is extracted from human cells (for example, lymphocytes) and electrophoresed on a sodium dodecyl sulfate-polyacrylamide gel. Where a protein-protein complex is to be identified (e.g., Hsp90-ZAP-70) the sample may be first treated to cross-link proteins in the sample. In another embodiment, the cellular protein is extracted from a leukemic cell. The proteins can be transferred to a membrane (for example, nitrocellulose or PVDF) by Western blotting, and the antibody preparation is incubated with the membrane. After washing the membrane to remove non-specifically bound antibodies, the presence of specifically bound antibodies is detected by the use of (by way of example) an anti-mouse antibody conjugated to an enzyme such as alkaline phosphatase. Application of an alkaline phosphatase substrate 5-bromo-4-chloro-3-indolyl phosphate/nitro blue tetrazolium results in the production of a dense blue compound by immunolocalized alkaline phosphatase. Antibodies that specifically detect the desired protein or complex will, by this technique, be visible at a given position on the determined by its molecular weight, which for ZAP-70 alone is about 70 kDa, Hsp90 alone is about 90 kDa, and for the combination is about 160 kDa (based on their individual deduced sequences and combination thereof).

In another embodiment, a first antibody that binds either Hsp90 or ZAP-70 is immobilized on a substrate. The sample is the incubated with the first antibody on the substrate under conditions that allow the antibody to bind to its specific target to obtain. Typically the bound antibody with be an anti-ZAP-20 antibody. The substrate is then washed and the antibody-antigen complex then contacted with a second antibody (typically an anti-Hsp90 antibody) that will bind to the second protein of the protein-protein pair (i.e., the Hsp90-ZAP-70 complex). For example, the antibody will bind to any Hsp90 protein linked to a ZAP-protein which is in-turn bound to an anti-ZAP-70 antibody on the substrate. A third antibody is then used to develop the substrate to detect the presence of the complex. A control will typically be used corresponding to desired concentrations of protein (e.g., Hsp90, ZAP-70 and/or a complex thereof).

In another aspect of the invention an immunoprecipitation method is used to determine the presence or amount of Hsp90-ZAP-70 complex in a sample. Immunoprecipitation methods are commonly used in the art.

As mentioned above, the invention also provides a threshold increase of ZAP-70 that is indicative of CLL or SLL and which reduces false negatives. In this particular aspect a threshold increase in ZAP-20 expression is set at approximately 20% more than a control sample (i.e., the amount of ZAP-20 in a subject that does not have CLL or SLL). For the purposes of quantitating the ZAP-70 protein, a biological sample of the subject, as described above and which includes cellular proteins, is used. Quantitation of ZAP-70 protein can be achieved by immunoassay (for example, by ELISA), immunohistochemistry, immunofluorescence, or flow cytometry and compared to levels of the protein found in healthy cells (e.g., cells from a subject that does not have CLL or SLL) followed by spectrophotometry or densitometry. A 20% or greater increase in the amount of ZAP-70 protein in the sample of a subject compared to the amount of ZAP-70 protein found in normal subject cells would be indicative of a leukemia.

The invention also provides methods for identifying modulators, e.g., test compounds or agents (e.g., antibodies, polypeptides, peptides, peptidomimetics, peptoids, small non-nucleic acid organic molecules, small inorganic molecules, oligonucleotides (such as antisense oligonucleotides, ribozymes, or siRNA), or other drugs) that bind to, disrupt or degrade an Hsp90-ZAP-70 complex (a polypeptide that interacts with an Hsp90-ZAP-70 complex can be assayed by co-precipitation). For example, a number of compounds have been identified that promote ZAP-70 degradation including, for example, 17-AAG and derivatives thereof (as discussed more fully herein). Modulatory effects on Hsp90-ZAP-70 can be determined by measuring, for example, apoptosis and/or BCR-signaling. For example, an agent that increases ZAP-70 degradation by disrupting the chaperone activity of Hsp90 will result in increased apoptosis in leukemia cells and/or a loss of BCR-signaling. Other effects that can be measured and that are indicative of an agent that modulates Hsp90-ZAP-70 include a reduction in phosphorylated $p72^{Syk}$, BLNK, and phospholipase-C$\gamma$; as well as a reduction in $Ca^{2+}$ flux. Compounds or agents thus identified can be used to treat cell proliferative disorder including leukemia in a therapeutic protocol, to elaborate the biological function of Hsp90 and/or ZAP-70.

A variety of isotopic and nonisotopic methods, e.g., calorimetric, enzymatic, and densitometric, afford sufficient sensitivity to evaluate the binding affinity of an inhibitor to a target protein. These methods are generally known in the art and can be used in the context of this invention.

The binding affinity of Hsp90 ligands to Hsp90 can be measured by the competitive binding assay described in Kamal et al., Nature 425:407-410, 2003. The binding affinity of the ligand is measured by its ability to inhibit the binding of geldanamycin, an inhibitor of Hsp90. The cell containing the Hsp90 is lysed in lysis buffer. The lysates are incubated with or without test agent and then incubated with biotin-geldanamycin linked to BioMag™ sreptavidin magnetic beads (Qiagen). The bound samples and the unbound supernatant can be separately collected and analyzed on SDS protein gels, and blotted using and Hsp90 antibody. The bands in the Western Blots may be quantitated using the Biorad Fluor-S MultiImager, and the percent inhibition of binding of Hsp90 to the biotin-geldanamycin calculated.

The downstream effect of Hsp90 can also be measured. For example, the effect on ZAP-70 by inhibition of Hsp90 can be directly measured by the amount of ZAP-70 expression or by determining the viability of the cells after treatment with selected Hsp90 inhibitors.

The invention provides methods of treating a subject with a cell proliferative disorder such as leukemia. Also provided are methods of prophylaxis and determination of risk factors by determining the amount of ZAP-70, activated Hsp90, and/or Hsp90-ZAP-70 complex in a sample from a subject.

The invention also provides a method of modulating apoptosis in a cell, the method comprising contacting an Hsp90 and/or ZAP-70 polypeptide with an agent that (i) inhibiting Hsp90 and/or ZAP-70 activity, (ii) inhibits or prevents the ability of Hsp90 and ZAP-70 to interact and/or (iii) inhibits the production of Hsp90 and/or ZAP-70.

The invention also provide a method of treating a subject with a cell proliferative disorder comprising contacting the subject with an agent that (i) inhibiting Hsp90 and/or ZAP-70 activity, (ii) inhibits or prevents the ability of Hsp90 and ZAP-70 to interact and/or (iii) inhibits the production of Hsp90 and/or ZAP-70.

The invention provides methods and compositions useful to modulate apoptosis in a cell, tissue and/or subject. "Apoptosis" refers to programmed cell death which occurs by an active, physiological process. Apoptosis plays an important role in developmental processes, including morphogenesis, maturation of the immune system, and tissue homeostasis whereby cell numbers are limited in tissues that are continually renewed by cell division. Apoptosis is an important cellular safeguard against tumorigenesis. An apoptotic cell or a cell going through "programmed cell death" exhibits one or more characteristics associated with timed or targeted cell death. Characteristics include inhibition of cell survival, growth, death or differentiation, protein/nucleic acid cleavage/fragmentation, chromatin condensation, membrane fragmentation, changes in expression or activity of one or more proteins that promote apoptosis or that inhibit apoptosis.

"Modulating" apoptosis means increasing, stimulating or inducing, or decreasing, inhibiting, blocking or preventing (e.g., prophylaxis) one or more characteristics of programmed cell death as described herein or known in the art. For example, the methods and compositions of the disclosure include agents (e.g., antisense molecules, ribozymes, polypeptides, small molecules, and the like) that increase, stimulate or induce apoptosis by inhibiting the activity of Hsp90, zeta-associated protein (ZAP) 70, or both Hsp90 and ZAP-70 and related proteins.

In one embodiment, the invention provides a method of modulating apoptosis by contacting Hsp90 and/or ZAP-70 with an agent that regulates the interaction of the Hsp90 and ZAP-70 to mediate apoptosis. As used herein, the term "interact" includes any detectable interactions between molecules. The term "interact" is also meant to include "binding" interactions between molecules. Interactions can, for example, be protein-protein, protein-nucleic acid, and nucleic acid-nucleic acid in nature including hydrogen-bond interactions, covalent-bond interactions and the like.

An "agent", as used herein, can be any molecule including, for example, a polypeptide, an antibody, a nucleic acid (e.g., an antisense, ribozyme, siRNA or the like) or a small molecule or drug agent. An agent can be a "therapeutic agent" useful for treating disorders associated with cell proliferation including anti-neoplastic agents and anti-inflammatory agents.

The invention provides apoptotic agents comprising agents that inhibit an anti-apoptotic affect of Hsp90 and/or ZAP-70. In one aspect of the invention, a small molecule is used to prevent the interaction, and/or disrupt the interaction of Hsp90 with a cytosolic component (e.g., a tyrosine kinase such as ZAP-70) thereby inhibiting an anti-apoptotic activity of Hsp90. In another aspect, agents are provided that inhibit transcription from an hsp (e.g., Hsp90) and/or ZAP-70 gene. In another aspect, inhibitory nucleic acid molecules (e.g., antisense, ribozymes, siRNA) molecules are used to inhibit the production of Hsp90 and/or ZAP-70. In one aspect, the apoptotic agents provide a method for inducing apoptosis by inhibiting the production of Hsp90 and/or ZAP-70 thereby inhibiting the anti-apoptotic affect of Hsp90 and/or ZAP-70 in a cell. The apoptotic agents of the invention are useful in treating neoplastic and cancer disorders by promoting apoptosis in cells expressing Hsp90 and/or ZAP-70.

In one embodiment where apoptotic activity is desired an apoptotic agent such as an Hsp90 and/or ZAP-70 antagonist is used. An Hsp90-inhibitor is one that disrupts the structure and/or function of an Hsp90 chaperone protein and/or a protein that is dependent on Hsp90. Hsp90 proteins comprise sequences as set forth in NCBI accession nos. P07900 and XM004515 (human α and β Hsp90, respectively), P11499 (Mus musculus), AAB2369 (rat), P46633 (Chinese hamster), JC1468 (chicken), AAF69019 (flesh fly), AAC21566 (zebrafish), AAD30275 (salnon), 002075 (Pig), NP015084 (yeast), and CAC29071 (frog). Grp94 and Trap-1 are related molecules falling within the definition of an Hsp90 as used herein. An Hsp90 inhibitor of the invention may be specifically directed against an Hsp90 of the specific host or patient or may be identified based on reactivity against an Hsp90 homolog from a different species or an Hsp90 variant.

In yet another aspect, the invention provides polypeptide antagonists of Hsp90 or ZAP-70 activity. Such polypeptides include antibodies, soluble domains of an Hsp90 or ZAP-70. By inhibiting the interaction of Hsp90 with a tyrosine kinase (e.g., ZAP-70) and/or by inhibiting the activation of Hsp90, apoptosis may be induced and the anti-apoptotic effect of Hsp90-ZAP-70 complex formation inhibited.

The invention also provides methods and compositions comprising small molecule and drug agents for the treatment of cell proliferative disorders such as CLL and SLL. In one aspect, the agent binds to the ATP site of Hsp90. For example, ansamycin antibiotics are natural products derived from *Streptomyces hygroscopicus* that have profound effects on eukaryotic cells. Many ansamycins, such as herbimycin A (HA) and geldanamycin (GM), bind tightly to a pocket in Hsp90 (Stebbins, C. et al., 1997, Cell, 89:239-250). The binding of ansamycins to Hsp90 has been reported to inhibit protein refolding and to cause the proteasome dependent degradation of a select group of cellular proteins (Sepp-Lorenzino, L., et al., 1995, J. Biol. Chem., 270:16580-16587; Whitesell, L. et al., 1994, Proc. Natl. Acad. Sci. USA, 91: 8324-8328).

Ansamycin compounds are characterized by having an "ansa" structure which comprises any one of benzoquinone, benzohydroquinone, naphthoquinone or napthohydroquinone moieties bridged by a long chain. Compounds of the naphthoquinone or naphthohydroquinone class are exemplified by the clinically important agents rifampicin and rifamycin, respectively. Compounds of the benzoquinone class are exemplified by geldanamycin (including its synthetic derivatives 17-alylamino-17-demethoxygeldanamycin (17-AAG), 17-N,N-dimethylaminoethylamino-17-demethoxygeldanamycin (DMAG), dihydrogeldanamycin and herbamycin). An example, of the benzohydroquinone class is macbecin.

The ansamycins were originally isolated on the basis of their ability to revert v-src transformed fibroblasts (Uehara, Y. et al., 1985, J. Cancer Res., 76: 672-675). Subsequently, they were said to have antiproliferative effects on cells transformed with a number of oncogenes, particularly those encoding tyrosine kinases (Uehara, Y., et al., 1988, Virology, 164: 294-98).

The use of ansamycins as anticancer agents is described in U.S. Pat. Nos. 4,261,989, 5,387,584 and 5,932,566. The preparation of the ansamycin, geldanamycin, is described in U.S. Pat. No. 3,595,955.

The ansamycin-binding pocket in the N-terminus of Hsp90 is highly conserved and has weak homology to the ATP-binding site of DNA gyrase (Stebbins, C. et al., supra; Grenert, J. P. et al., 1997, J. Biol. Chem., 272:23843-50). This pocket has been reported to bind ATP and ADP with low affinity and to have weak ATPase activity (Proromou, C. et al., 1997, Cell, 90: 65-75; Panaretou, B. et al., 1998, EMBO J., 17: 4829-36). In vitro and in vivo studies indicate that occupancy of the pocket by ansamycins alters Hsp90 function and inhibits protein refolding. At high concentrations, ansamycins have been reported to prevent binding of protein substrates to Hsp90 (Scheibel, T., H. et al., 1999, Proc. Natl. Acad. Sci. USA 96:1297-302; Schulte, T. W. et al., 1995, J. Biol. Chem. 270:24585-8; Whitesell, L., et al., 1994, Proc. Natl. Acad. Sci. USA 91:8324-8328). Alternatively, they have also been reported to inhibit the ATP-dependent release of chaperone-associated protein substrates (Schleider, C., L. et al., 1996, Proc. Natl. Acad. Sci. USA, 93:14536-41; Sepp-Lorenzino et al., 1995, J. Biol. Chem. 270:16580-16587). In both models, the unfolded substrates are said to be degraded by an ubiquitin-dependent process in the proteasorne (Schneider, C., L., supra; Sepp-Lorenzino, supra.)

In both tumor and nontransformed cells, binding of ansamycins to Hsp90 has been reported to result in the degradation of a subset of signaling regulators. These include Raf (Schulte, T. W. et al., 1997, Biochem. Biophys. Res. Commun. 239:655-9; Schulte, T. W., et al., 1995, J. Biol. Chem. 270:24585-8), nuclear steroid receptors (Segnitz, B., and U. Gehring. 1997, J. Biol. Chem. 272:18694-18701; Smith, D. F. et al., 1995, Mol. Cell. Biol. 15:6804-12), v-src (Whitesell, L., et al., 1994, Proc. Natl. Acad. Sci. USA 91:8324-8328) and certain transmembrane tyrosine kinases (Sepp-Torenzino, L. et al., 1995, J. Biol. Chem. 270:16580-16587) such as EGF receptor (EGFR) and Her2/Neu (Hartmaann, F., et al., 1997, Int. J. Cancer 70:221-9; Miller, P. et al., 1994, Cancer Res. 54:2724-2730; Mimnaugh, E. G., et al., 1996, J. Biol. Chem. 271:22796-801; Schnur, R. et al., 1995, J. Med. Chem. 38:3806-3812). The ansamycin-induced loss of these proteins is said to lead to the selective disruption of certain regulatory pathways and results in growth arrest at specific phases of the cell cycle (Muise-Heimericks, R. C. et al., 1998, J. Biol. Chem. 273:29864-72). Other useful agents that inhibit Hsp90 function include geldanamycin, 17AAG, and radicicol.

Inhibition of cell growth is associated with apoptosis and, in certain cellular systems, with induction of differentiation (Vasilevskaya, A. et al., 1999, Cancer Res., 59: 3935-40). A geldanamycin derivative is currently in clinical trials.

The invention provides methods and compositions useful for suppression of Hsp90 and/or ZAP-70 expression or function as a novel approach to cancer therapy, particularly leukemia. For example, geldanamycin is a potent Hsp90 inhibitor which is capable of inhibiting the heat shock response, inhibit the growth of carcinogen-induced tumors in rats and in human leukemia cells transplanted into mice. Treatment of breast cancer cells with geldanamycin, an anti-proliferative agent, enables the degradation of p185 in the breast cancer cells by disrupting the association of GRP94-p185 complexes. The invention demonstrates that Hsp90 inhibitors downmodulate the expression and function of the zeta-associated protein-70 (ZAP-70) protein in chronic lymphocytic leukemia (CLL) cells.

In one aspect of the invention, a method of treating a form of CLL or SLL which is characterized by the expression of ZAP-70 in a B-cell is provided. The method includes administering to a subject in need thereof a pharmaceutical effective amount of an Hsp90 inhibitor. In one embodiment, the inhibitor binds at the ATP-binding site of an Hsp90 protein.

In one embodiment, the inhibitor belongs to a structural compound selected from the group consisting of purines, purine analogs, heterocyclics, ansamycins, radicicol, zearalanols, ATP analogs, indoles, chalcones, and benzimidazoles. In another embodiment, the inhibitor is an ansamycin including those described herein or a polymorph, solvate, ester, tautomer, enantiomer, pharmaceutically acceptable salt or prodrug thereof. Examples of such ansamycin compounds include:

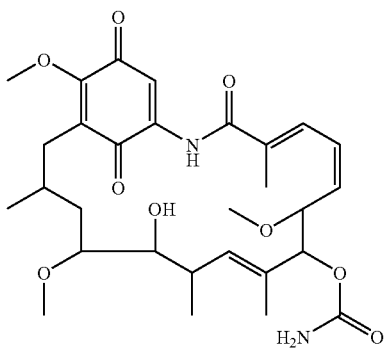

Geldanamycin

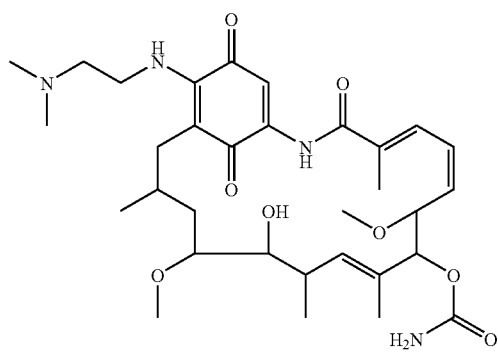

DMAG

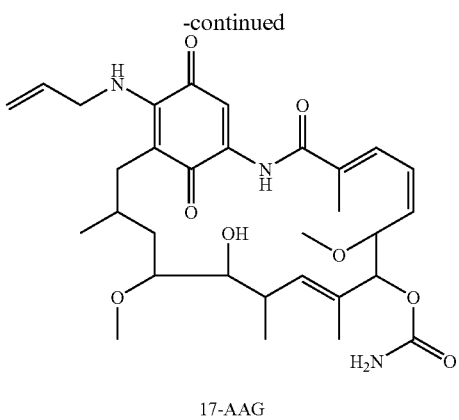

17-AAG

In a further embodiment, the ansamycin is 17-allylamino-17-demethoxygeldanamycin (17-AAG) or 17-(2-dimethylaminoethy)amino-17-demethoxygeldanamycin (17-DMAG) which may comprise low melt forms of 17-AAG, high melt forms, and/or amorphous forms of 17-AAG.

The invention also includes reduced forms of 17-AAG (17-allylamino-18,21-dihydro-17-de-methoxygeldanamycin), as well as members of the 18,21-dihydro-geldanamycin family including, but not limited to, 18,21-dihydro analogs of 17-Amino-4,5-dihydro-17-demethoxy-geldanamycin; 17-Methylamino-4,5-dihydro-17-demethoxygeldanamycin; 17-Cyclopropylamino-4,5-dihydro-17-demethoxygeldanarnycin; 17-(2'-Hydroyethylamino)-4,5-dihydro-17-demethoxygelclanamycin; 17-(2-Methoxyethylamino)-4,5-dihydro-17-demethoxygeldanamycin; 17-(2'-Fluoroethylamino)-4,5-dihydro-17-demethoxygeldanamycin; 17-(S)-(+)-2-Hydroxypropylamino-4,5-dihydro-17-demethoxygeldanamycin; 17-Azetidin-1-yl-4,5-dihydro-17-demethoxygeldanamycin; 17-(3-Hydroxyazetin-1-yl)-4,5-dihydro-17-demethoxygeldanamycin; 17-Azetidin-1-yl-4,5-dihydro-11-alpha-fluoro-17-demethoxygeldamycin; 17-(2'-Cyanoethylamino)-17-demethoxygeldanamycin; 17-(2'-Fluoroethylamino-)-17-demethoxygeldanamycin; 17-Amino-22-(2'-methoxyphenacyl)-17-demethoxygeldanamycin; 17-Amino-22-(3'-methoxyphenacyl)-17-demethoxygeldanetmycin, 17-Amino-22-(4'-chlorophenacyl)-17-demethoxygeldanamycin; 17-Amino-22-(3',4'-dichlorophenacyl)-17-demethoxygeldanamycin, 17-Amino-22-(4'-amino-3'-iodophenacyl)-17-demethoxygeldanamycin; 17-Amino-22-(4'-azido-3'-iodophenacyl)-17-demethoxygeldanamycin; 17-Amino-11-alpha-fluoro-17-demethoxygeldanamycin; 17-Allylamino-11-alpha-fluoro-17-demethoxygeldanamycin; 17-Propargylamino-11-alpha-fluoro-17-demethoxygeldanamycin; 17-(2'-Fluoroethylamino)-11-alpha-fluoro-17-demethoxygeldanamycin; 17-Azetidin-1-yl-11-(4'-azidophenyl)sulfamylcarbonyl-17-demethoxygeldanamycin; 17-(2'-Fluoroethylamino)-11-keto-17-demethoxygeldanamycin; 17-Azetidin-1-yl-11-keto-17-demethoxygeldanamycin; and 17-(3'-Hydroxyazetidin-1-yl)-11-keto-17-demethoxygeldanamycin. (see also U.S. Patent Publication No. 20050227955 for other 17-AAG analogs and derivatives that can be used in the methods and compositions of the invention).

Accordingly, the invention provides methods and compositions useful in reducing the anti-apoptotic effect of Hsp90 and/or ZAP-70, increase sensitivity of cancer cells to chemotherapeutic agents, and promote apoptosis of neoplastic cells.

The methods and compositions of the invention inhibit the production or activity of Hsp90 and/or ZAP-70 in neoplastic cells (e.g., cancer cells) and tissues. More particularly, the methods and compositions inhibit the anti-apoptotic effects resulting from Hsp90 chaperoning of ZAP-70 protein.

The invention provides methods and compositions that are useful to promote apoptosis in a tissue or cell comprising contacting the tissue or cell with an agent that inhibits the anti-apoptotic activity of an Hsp90 and/or ZAP-70. The methods and compositions are useful in treating neoplastic disorders including cancer and tumor growth and more specifically leukemia (e.g., lymphocytic leukemia). The methods and compositions can be used alone or in combination with other neoplastic/cancer/leukemia therapies. For example, the methods and compositions of the invention can be used in combination with chemotherapeutic drugs such as, but not limited to, 5-fluorouracil (5FU), cytosine arabinoside, cyclophosphamide, cisplatin, carboplatin, doxyrubicin, etoposide, taxol, and alkylating agents. Furthermore, combinations of nucleic acid inhibitors may be used.

Methods of the invention may also involve recombinant forms of the Hsp90 and/or ZAP-70 proteins. In a one embodiment, variant Hsp90 or ZAP-70 proteins lack one or more functional activities of a native Hsp90 or ZAP-70 protein.

Hsp90 or ZAP-70 protein variants can be generated through various techniques known in the art. For example, Hsp90 or ZAP-70 protein variants can be made by mutagenesis, such as by introducing discrete point mutation(s), or by truncation. Mutation can give rise to an Hsp90 or ZAP-70 protein variant having substantially the same, or merely a subset of the functional activity of a native Hsp90 or ZAP-70 protein. Alternatively, antagonistic forms of the protein can be generated which are able to inhibit the function of the naturally occurring form of the protein, such as by competitively binding to another molecule that interacts with Hsp90 or ZAP-70 protein. Other variants of Hsp90 or ZAP-70 proteins that can be generated include those that are resistant to proteolytic cleavage, as fox example, due to mutations that alter protease target sequences. Whether a change in the amino acid sequence of a peptide results in an Hsp90 or ZAP-70 protein variant having one or more functional activities of a native Hsp90 or ZAP-70 protein can be readily determined by testing the variant for a native Hsp90 or ZAP-70 protein functional activity.

In another aspect, a library of coding sequence fragments can be provided for a Hsp90 or ZAP-70 clone in order to generate a variegated population of Hsp90 or ZAP-70 polypeptide fragments for screening and subsequent selection of fragments having one or more antagonist (e.g., apoptotic) activities. A variety of techniques are known in the art for generating such libraries, including chemical synthesis. In one embodiment, a library of coding sequence fragments can be generated by (i) treating a double-stranded PCR fragment of a Hsp90 or ZAP-70 polynucleotide coding sequence with a nuclease under conditions wherein nicking occurs only about once per molecule; (ii) denaturing the double-stranded DNA; (iii) renaturing the DNA to form double-stranded DNA which can include sense/antisense pairs from different nicked products; (iv) removing single-stranded portions from reformed duplexes by treatment with S1 nuclease; and (v) ligating the resulting fragment library into an expression vector. By this exemplary method, an expression library can be derived which codes for N- and C-terminal and internal fragments of various sizes.

A wide range of techniques are known in the art for screening products of combinatorial libraries made by point mutations or truncation, and for screening cDNA libraries for products having a certain property. Such techniques will be generally adaptable for rapid screening of the gene libraries generated by the combinatorial mutagenesis of Hsp90 or ZAP-70 polynucleotide variants. The most widely used techniques for screening large libraries typically involve cloning the library into replicable expression vectors, transforming appropriate cells with the resulting library of vectors, and expressing the combinatorial genes under conditions in which detection of a desired activity facilitates relatively easy isolation of the vector encoding the gene whose product was detected. One screening technique useful to measure anti-apoptotic and apoptotic effects includes determining cell survival in the presence of etoposide. Recombinant products that inhibit (e.g., are antagonistic of) native Hsp90 or ZAP-70 function will show an increase in cell-death. Thus, the invention provides methods of mutagenizing and screening gene products to determine their agonistic and/or antagonistic effect on Hsp90 or ZAP-70 activity. Agents that have antagonistic effects are useful to treat diseases and disorders having unwanted cell growth (e.g., cell proliferative disorders associated with cancer and the like).

Methods of the invention may utilize mimetics, e.g. peptide or non-peptide agents, that are able to disrupt binding of an Hsp90 with a ZAP-70 protein or inhibit the activation of Hsp90 by interacting with an ATP binding site on Hsp90 thereby preventing ATP from interacting with Hsp90.

The invention provides methods involving modulating levels of Hsp90 or ZAP-70 in a cell. The cell may be in vitro or in vivo. Where the cell is in vivo it may be present in an animal subject such as any mammal including humans, rats, mice, cats, dogs, goats, sheep, horses, monkeys, apes, rabbits, cattle, and the like. The animal subject can be in any stage of development including adults, young animals, and neonates. Animal subjects also include those in a fetal stage of development. Target tissues can be any within the animal subject such as liver, kidney, heart (e.g., cardiomyocytes), lungs, components of gastrointestinal tract, pancreas, gall bladder, urinary bladder, skeletal muscle, the central nervous system including the brain, eye, skin, bones, and the like.

A variety of well-known techniques can be used to identify polypeptides which specifically bind to, for example, Hsp90 or ZAP-70, and regulate their interactions. Exemplary techniques include mobility shift DNA-binding assays, methylation and uracil interference assays, DNase and hydroxy radical footprinting analysis, fluorescence polarization, and UV crosslinking or chemical cross-linkers. Furthermore, biological assays the measure the agonistic and antagonistic effects of such agents are also provided.

In another aspect, an apoptotic nucleic acid agent is used. An apoptotic nucleic acid agent can be an antisense nucleic acid that hybridizes to mRNA encoding a Hsp90 or a ZAP-70 protein. Antisense nucleic acid molecules for use with the invention are those that specifically hybridize under cellular conditions to cellular mRNA and/or genomic DNA encoding an Hsp90 or ZAP-70 protein in a manner that inhibits expression of the protein(s), e.g., by inhibiting transcription and/or translation. The binding may be by conventional base pair complementarity, or, for example, in the case of binding to DNA duplexes, through specific interactions in the major groove of the double helix.

Antisense constructs can be delivered as an expression plasmid which, when transcribed in the cell, produces RNA which is complementary to at least a unique portion of the mRNA and/or endogenous gene which encodes an Hsp90 or ZAP-70 protein. Alternatively, the antisense construct can take the form of an oligonucleotide probe generated ex vivo which, when introduced into a Hsp90 and ZAP-70 protein expressing cell, causes inhibition of Hsp90 or ZAP-70 protein expression by hybridizing with an mRNA and/or genomic DNA coding for an Hsp90 and/or ZAP-70 protein. Such antisense molecules may comprise modified nucleotides that are resistant to endogenous nucleases, e.g., exonucleases and/or endonucleases, and are therefore stable in vivo. Additionally, general approaches to constructing oligomers useful in antisense therapy have been reviewed, for example, by Van der Krol et al., Biotechniques 6:958-976, 1988; and Stein et al., Cancer Res. 48:2659-2668, 1988.

Antisense approaches involve the design of nucleic acid molecules (e.g., DNA, RNA, or modified forms thereof) that are complementary to nucleic acids encoding an Hsp90 or ZAP-70 protein. The antisense molecules will bind to Hsp90 or ZAP-70 mRNA transcripts and prevent translation or to the endogenous gene and prevent transcription. Absolute complementarity is not required. The ability to hybridize will depend on both the degree of complementarity and the length of the antisense nucleic acid. Generally, the longer the hybridizing nucleic acid, the more base mismatches it may contain and still form a stable duplex (or triplex, as the case may be). One skilled in the art can ascertain a tolerable degree of mismatch by use of standard procedures to determine the melting point of the hybridized complex.

Antisense nucleic acid molecules that are complementary to the 5' end of an mRNA, e.g., the 5' untranslated sequence up to and including the AUG initiation codon, should work most efficiently at inhibiting translation. However, sequences complementary to the 3' untranslated region of mRNAs have been shown to be effective at inhibiting translation of mRNAs as well. (Wagner, R., Nature 372:333, 1994). Therefore, antisense molecules complementary to either the 5' or 3' untranslated, non-coding regions of a Hsp90 or ZAP-70 mRNA or gene may be used in an antisense approach to inhibit transcription and/or translation of endogenous Hsp90 or ZAP-70 gene or mRNA, respectively. Oligonucleotides complementary to the 5' untranslated region of the mRNA should include the complement of the AUG start codon.

The coding strand sequences of Hsp90 and/or ZAP-70 are known. Given the coding strand sequences, antisense nucleic acids can be designed according to the rules of Watson and Crick base pairing. The antisense nucleic acid molecule can be complementary to the entire coding region of an Hsp90 or ZAP-70 polynucleotide, or can be an oligonucleotide, which is antisense to only a portion of the coding or noncoding region of an Hsp90 or ZAP-70. For example, the antisense oligonucleotide can be complementary to the region surrounding the transcriptional or translation start site of Hsp90 or ZAP-70 mRNA. An antisense oligonucleotide can be, for example, about 10, 20, 25, 50, 100, 150, 200, 250, 300, 350, 400 or more nucleotides in length. An antisense nucleic acid molecule can be constructed using chemical synthesis and enzymatic ligation reactions using procedures known in the art. Antisense nucleic acid molecules of the invention may be synthesized by standard methods known in the art, e.g. by use of an automated DNA synthesizer (such as are commercially available from Biosearch, Applied Biosystems). As examples, phosphorothioate oligonucleotides may be synthesized by the method of Stein et al., Nucl. Acids Res. 16:3209, 1988; or methylphosphonate oligonucleotides can be prepared by use of controlled pore glass polymer supports (Sarin et al., Proc. Natl. Acad. Sci. U.S.A. 85:7448-7451, 1988). An antisense nucleic acid molecule can be chemically synthesized using naturally occurring nucleotides or variously modified nucleotides designed to increase the biological stability of the molecules or to increase the physical stability of the duplex formed between the antisense and sense nucleic acids.

The invention includes antisense nucleic acid molecules, which hybridize with a polynucleotide sequence comprising a sequence encoding an Hsp90 or ZAP-70 protein. The antisense molecules employed may be unmodified or modified RNA or DNA molecules. Suitable modifications include, but are not limited to, the ethyl or methyl phosphonate modification disclosed in U.S. Pat. No. 4,469,863, the disclosure of which is incorporated by reference, and the phosphorthioate modifications to deoxynucleotides described by LaPlanche, et al., 1986 Nucleic Acids Research, 14:9081, and by Stec, et al., 1984 J. Am. Chem Soc. 106:6077. The modification to the antisense oligonucleotides is typically a terminal modification in the 5' or 3' region. Alternatively, the antisense molecules can have chimeric backbones of two or more modified nucleic acid bases, which are modified by different methods. Such methods include, for example, amino acid or nucleic acid modification as described by K. Ramasamy and W. Seifert (Bioorganic and Medicinal Chemistry Letters, 6(15): 1799-1804 (1996)) or 4' sugar substituted olignucleotides described by G. Wang and W. Seifert (Tetrahedron Letters, 37(36):6515-6518 (1996)).

Phosphodiester-linked oligonucleotides are particularly susceptible to the action of nucleases in serum or inside cells, and therefore in one embodiment the antisense nucleic acid molecules of the invention are phosphorothioate or methyl phosphonate-linked analogues, which have been shown to be nuclease-resistant. Specific examples of some antisense oligonucleotides envisioned for this invention may contain phosphorothioates, phosphotriesters, methyl phosphonates, short chain alkyl or cycloalkyl intersugar linkages or short chain heteroatomic or heterocyclic intersugar ("backbone") linkages. Typical are phosphorothioates and those with $CH_2NHOCH_2$, $CH_2N(CH_3)OCH_2$, $CH_2ON(CH_3)CH_2$, $CH_2N(CH_3)N(CH_3)CH_2$ and $ON(CH_3)CH_2CH_2$ backbones (where phosphodiester is $OPOCH_2$). Also typical are oligonucleotides having morpholino backbone structures (Summerton and Weller, U.S. Pat. No. 5,034,506). In other embodiments, 2'-methylribonucleotides (Inoue, et al., Nucleic Acids Research, 15:6131, 1987) and chimeric oligonucleotides that are composite RNA-DNA analogues (Inoue, et al., FEBS Lett., 215:327, 1987) may also be used for the purposes described herein. Finally, DNA analogues, such as peptide nucleic acids (PNA) are also included (Egholm, et al., Nature 365:566, 1993; Nielsen et al., Science, 254:1497, 1991) can be used according to the invention. Other oligonucleotides may contain alkyl and halogen-substituted sugar moieties comprising one of the following at the 2' position: OH, SH, $SCH_3$, F, OCN, $OCH_3OCH_3$, $OCH_3O(CH_2)nCH_3$, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O, S, or N-alkyl; O, S or N alkenyl; $SOCH_3$; $SO_2CH_3$; $ONO_2$; $NO_2$; $N_3$; $NH_2$; heterocloalkyl; heterocycloalkaryl; aminoalkylamino; polyalkylamino; substituted silyl; an RNA cleaving group; a cholesteryl group; a conjugate; a reporter group; an intercalator; a group for improving the pharmacokinetic properties of a oligonucleotide; or a group for improving the pharmacodynamic properties of a oligonucleotide and other substituents having similar properties. Oligonucleotides may also have sugar mimetics such as cyclobutyls in place of the pentofuranosyl group. Other embodiments may include at least one modified base form or "universal base" such as inosine. The preparation of base-modified nucleosides, and the synthesis of modified oligonucleotides using said base-modified nucleosides as precursors, has been described, for example, in U.S. Pat. Nos. 4,948,882 and 5,093,232. These base-modified nucleosides have been designed so that they can be incorporated by chemical synthesis into either terminal or internal positions of an oligonucleotide. Such base-modified nucleosides, present at either terminal or internal positions of an oligonucleotide, can serve as sites for attachment of a peptide or other antigen. Nucleosides modified in their sugar moiety have also been described (e.g., U.S. Pat. No. 5,118,802 and U.S. Pat. No. 5,681,940, both of which are incorporated by reference) and can be used similarly. Persons of ordinary skill in this art will be able to select other linkages for use in the invention. These modifications also may be designed to improve the cellular uptake and stability of the oligonucleotides. It is understood that depending on the route or form of administration of the antisense oligonucleotides of the invention, the modification or site of modification will vary (e.g., 5' or 3' modification). One of skill in the art can readily determine the appropriate modification.

Examples of modified nucleotides which can be used to generate the antisense molecules include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N_6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense molecule can be produced biologically using an expression vector into which an Hsp90 or ZAP-70 polynucleotide or fragment thereof has been subcloned in an antisense orientation (i.e., RNA transcribed from the inserted nucleic acid will be of an antisense orientation to a target nucleic acid of interest).

Small double stranded nucleic acid molecules that can silence an Hsp90 or ZAP-70 are also provided as part of the invention. Small interfering RNA (siRNA) molecules are provided that interfere with RNA transcription. RNA interference (RNAi) is a mechanism of post-transcriptional gene silencing in which double-stranded RNA (dsRNA) corresponding to a gene (or coding region) of interest is introduced into a cell or an organism, resulting in degradation of the corresponding mRNA. The RNAi effect persists for multiple cell divisions before gene expression is regained. RNAi is therefore an extremely powerful method for making targeted knockouts or "knockdowns" at the RNA level. RNAi has proven successful in human cells, including human embryonic kidney and HeLa cells (see, e.g., Elbashir et al., Nature, 411(6836):494-8, 2001). In one embodiment, Hsp90 or ZAP-70 silencing can be induced in mammalian cells by enforcing endogenous expression of RNA hairpins (see Paddison et al., PNAS USA 99:1443-1448, 2002). In another embodiment, transfection of small (21-23 nt) dsRNA specifically inhibits gene expression (reviewed in Caplen, Trends in Biotechnology 20:49-51, 2002).

Briefly, dsRNA corresponding to a portion of an Hsp90 or ZAP-70 gene to be silenced is introduced into a cell. The dsRNA can comprise longer sequences that are subsequently digested into 21-23 nucleotide siRNAs, or short interfering RNAs, or the 21-23 nucleotide siRNA molecules may be directly provided to the cell. The siRNA duplexes bind to a nuclease complex to form what is known as the RNA-induced silencing complex, or RISC. The RISC targets the homologous transcript by base pairing interactions between one of the siRNA strands and the endogenous mRNA. It then cleaves the mRNA about 12 nucleotides from the 3' terminus of the siRNA (reviewed in Sharp et al., Genes Dev 15: 485-490, 2001; and Hammond et al., Nature Rev Gen 2: 110-119, 2001).

RNAi technology in gene silencing utilizes standard molecular biology methods. dsRNA corresponding to the sequence from a target gene to be inactivated can be produced by standard methods, e.g., by simultaneous transcription of both strands of a template DNA (corresponding to the target sequence) with T7 RNA polymerase. Kits for production of dsRNA for use in RNAi are available commercially, e.g., from New England Biolabs, Inc. Methods of transfection of dsRNA or plasmids engineered to make dsRNA are routine in the art.

Gene silencing effects similar to those of RNAi have been reported in mammalian cells with transfection of a mRNA-cDNA hybrid construct (Lin et al., Biochem Biophys Res Commun, 281(3):639-44, 2001), providing another strategy of gene silencing.

Accordingly, the invention provides small interfering nucleic acids (siNA) that interact with a polynucleotide encoding an Hsp90 or ZAP-70.

Ribozyme molecules designed to catalytically cleave Hsp90 or ZAP-70 mRNA transcripts can also be used to prevent translation of Hsp90 or ZAP-70 mRNA and expression of Hsp90 or ZAP-70 protein (see, e.g., PCT Publication No. WO 90/11364, published Oct. 4, 1990; Sarver et al., Science 247:1222-1225, 1990 and U.S. Pat. No. 5,093,246). While ribozymes that cleave mRNA at site specific recognition sequences can be used to destroy Hsp90 or ZAP-70 mRNAs, the use of hammerhead ribozymes is typical. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585-591, 1988. Typically the ribozyme is engineered so that the cleavage recognition site is located near the 5' end of Hsp90 or ZAP-70 mRNA; i.e., to increase efficiency and minimize the intracellular accumulation of non-functional mRNA transcripts. Ribozymes within the invention can be delivered to a cell using a vector.

Endogenous Hsp90 or ZAP-70 gene expression can also be reduced by inactivating or "knocking out" the Hsp90 or ZAP-70 gene or its promoter using targeted homologous recombination. See, e.g., Kempin et al., Nature 389: 802 (1997); Smithies et al., Nature 317:230-234, 1985; Thomas and Capecchi, Cell 51:503-512, 1987; and Thompson et al., Cell 5:313-321, 1989. For example, a mutant, non-functional Hsp90 or ZAP-70 gene variant (or a completely unrelated DNA sequence) flanked by DNA homologous to the endogenous Hsp90 or ZAP-70 gene (either the coding regions or regulatory regions of the Hsp90 or ZAP-70 gene) can be used, with or without a selectable marker and/or a negative selectable marker, to transfect cells that express Hsp90 or ZAP-70 protein in vivo.

The nucleic acids, ribozyme, RNAi, and triple helix molecules used in the invention may be prepared by any method known in the art for the synthesis of DNA and RNA molecules. These include techniques for chemically synthesizing oligodeoxyribonucleotides and oligoribonucleotides well known in the art such as for example solid phase phosphoramide chemical synthesis. Alternatively, RNA molecules may be generated by in vitro and in vivo transcription of DNA sequences encoding the nucleic acid molecule. Such DNA sequences may be incorporated into a wide variety of vectors, which incorporate suitable RNA polymerase promoters. Alternatively, antisense cDNA constructs that synthesize antisense RNA constitutively or inducibly, depending on the promoter used, can be introduced stably into cell lines.

Various techniques using viral vectors for the introduction of a Hsp90 or ZAP-70 inhibitory nucleic acids (e.g., an antisense molecule) into a cell may be utilized in the methods of the invention. Viral vectors for use in the invention are those that exhibit low toxicity to a host cell and induce production of therapeutically useful quantities of antisense and/or RNAi nucleic acids in a tissue-specific manner. Viral vector methods and protocols that may be used in the invention are reviewed in Kay et al. Nature Medicine 7:33-40, 2001. The use of specific vectors, including those based on adenoviruses, adeno-associated viruses, herpes viruses, and retroviruses are described in more detail below.

The use of recombinant adenoviruses as gene therapy vectors is discussed in W. C. Russell, Journal of General Virology 81:2573-2604, 2000; and Bramson et al., Curr. Opin. Biotechnol. 6:590-595, 1995. Adenovirus vectors are useful in the invention because they (1) are capable of highly efficient gene expression in target cells and (2) can accommodate a relatively large amount of heterologous (non-viral) DNA. A typical form of recombinant adenovirus is a "helper-dependent" adenovirus vector. Such a vector features, for example, (1) the deletion of all or most viral-coding sequences (those sequences encoding viral proteins), (2) the viral inverted terminal repeats (ITRs) which are sequences required for viral DNA replication, (3) up to 28-32 kb of "exogenous" or "heterologous" sequences (e.g., sequences encoding an antisense molecule, or an RNAi molecule), and (4) the viral DNA packaging sequence which is required for packaging of the viral genomes into infectious capsids.

Other viral vectors that might be used in the invention are adeno-associated virus (AAV)-based vectors. AAV-based vectors are advantageous because they exhibit high transduction efficiency of target cells and can integrate into the host genome in a site-specific manner. Use of recombinant AAV vectors is discussed in detail in Tal, J., J. Biomed. Sci. 7:279-291, 2000 and Monahan and Samulski, Gene Therapy 7:24-30, 2000. A typical AAV vector comprises a pair of AAV inverted terminal repeats (ITRs) which flank at least one cassette containing a tissue or cell specific promoter operably linked to a Hsp90 or ZAP-70 inhibitory nucleic acid. The DNA sequence of the AAV vector, including the ITRs, the promoter and Hsp90 or ZAP-70 gene may be integrated into the host genome.

The use of herpes simplex virus (HSV)-based vectors is discussed in detail in Cotter and Robertson, Curr. Opin. Mol. Ther. 1:633-644, 1999. HSV vectors deleted of one or more immediate early genes (IE) are advantageous because they are generally non-cytotoxic, persist in a state similar to latency in the host cell, and afford efficient host cell transduction. Recombinant HSV vectors can incorporate approximately 30 kb of heterologous nucleic acid. A typical HSV vector is one that: (1) is engineered from HSV type I, (2) has its IE genes deleted, and (3) contains a tissue-specific promoter operably linked to a Hsp90 or ZAP-70 inhibitory nucleic acid (e.g., an antisense, RNAi, Hsp90 or ZAP-70 variant). HSV amplicon vectors may also be useful in various methods of the invention. Typically, HSV amplicon vectors are approximately 15 kb in length, and possess a viral origin of replication and packaging sequences.

Retroviruses such as C-type retroviruses and lentiviruses are also useful in the invention. For example, retroviral vectors may be based on murine leukemia virus (MLV). See, e.g., Hu and Pathak, Pharmacol. Rev. 52:493-511, 2000 and Fong et al., Crit. Rev. Ther. Drug Carrier Syst. 17:1-60, 2000. MLV-based vectors may contain up to 8 kb of heterologous nucleic acids in place of the viral genes. The nucleic acids typically comprise a tissue-specific promoter and a Hsp90 or ZAP-70 inhibitory nucleic acid.

Additional retroviral vectors that might be used are replication-defective lentiviruses-based vectors, including human immunodeficiency (HIV)-based vectors. See, e.g., Vigna and Naldini, J. Gene Med. 5:308-316, 2000 and Miyoshi et al., J. Virol. 72:8150-8157, 1998. Lentiviral vectors are advantageous in that they are capable of infecting both actively dividing and non-dividing cells. They are also highly efficient at transducing human epithelial cells. Lentiviral vectors for use in the invention may be derived from human and non-human (including SUV) lentiviruses. A typical lentiviral vector includes nucleic acid sequences required for vector propagation as well as a tissue-specific promoter operably linked to a Hsp90 or ZAP-70 inhibitory nucleic acid.

A lentiviral vector may be packaged into any suitable lentiviral capsid. The substitution of one particle protein with another from a different virus is referred to as "pseudotyping". The vector capsid may contain viral envelope proteins from other viruses, including murine leukemia virus (MLV) or vesicular stomatitis virus (VSV). The use of the VSV G-protein yields a high vector titer and results in greater stability of the vector virus particles.

Alphavirus-based vectors, such as those made from semliki forest virus (SFV) and sindbis virus (SIN), might also be used in the invention. Use of alphaviruses is described in Lundstrom, K., Intervirology 43:247-257, 2000 and Perri et al., Journal of Virology 74:9802-9807, 2000. Alphavirus vectors typically are constructed in a format known as a replicon. A replicon may contain (1) alphavirus genetic elements required for RNA replication, and (2) a heterologous nucleic acid such as one encoding a Hsp90 or ZAP-70 inhibitory nucleic acid.

Recombinant, replication-defective alphavirus vectors are advantageous because they are capable of high-level gene expression, and can infect a wide host cell range. Alphavirus replicons may be targeted to specific cell types by displaying on their virion surface a functional ligand or binding domain that would allow selective binding to target cells expressing a cognate binding partner. Alphavirus replicons may establish latency, and therefore long-term heterologous nucleic acid expression in a host cell. The replicons may also exhibit transient heterologous nucleic acid expression in the host cell. To increase tissue selectivity of the virus and reduce risk not only can such a virus have a targeted ligand on the virion surface, but also the heterologous nucleic acid (e.g., a Hsp90 or ZAP-70 inhibitory nucleic acid) can be operably linked to a tissue specific promoter.

In addition to viral vector-based methods, non-viral methods may also be used to introduce a Hsp90 or ZAP-70 inhibitory nucleic acid into a host cell. A review of non-viral methods of gene delivery is provided in Nishikawa and Huang, Human Gene Ther. 12:861-870, 2001. A non-viral gene delivery method according to the invention employs plasmid DNA to introduce a Hsp90 or ZAP-70 inhibitory nucleic acid into a cell. Plasmid-based gene delivery methods are generally known in the art and are described in references such as Ilan, Y., Curr. Opin. Mol. Ther. 1:116-120, 1999, Wolff, J. A., Neuromuscular Disord. 7:314-318, 1997 and Arztl, Z., Fortbild Qualitatssich 92:681-683, 1998.

Methods involving physical techniques for introducing a Hsp90 or ZAP-70 inhibitory nucleic acid into a host cell can be adapted for use in the invention. For example, the particle bombardment method of gene transfer utilizes an Accell device (gene gun) to accelerate DNA-coated microscopic gold particles into a target tissue, e.g., a cancer tissue. See, e.g., Yang et al., Mol. Med. Today 2:476-481 1996 and Davidson et al., Rev. Wound Repair Regen. 6:452-459, 2000. As another example, cell electropermeabilization (also termed cell electroporation) may be employed to deliver a Hsp90 or ZAP-70 inhibitory nucleic acids into cells. See, e.g., Preat, V., Ann. Pharm. Fr. 59:239-244 2001.

Synthetic gene transfer molecules can be designed to form multimolecular aggregates with plasmid DNA. These aggregates can be designed to bind to a target cell surface in a manner that triggers endocytosis and endosomal membrane disruption. Cationic amphiphiles, including lipopolyamines and cationic lipids, may be used to provide receptor-independent nucleic acid transfer into target cells. In addition, preformed cationic liposomes or cationic lipids may be mixed with plasmid DNA to generate cell-transfecting complexes. Methods involving cationic lipid formulations are reviewed in Felgner et al., Ann. N.Y. Acad. Sci. 772:126-139, 1995 and Lasic and Templeton, Adv. Drug Delivery Rev. 20:221-266, 1996. For gene delivery, DNA may also be coupled to an amphipathic cationic peptide (Fominaya et al., J. Gene Med. 2:455-464, 2000).

DNA microencapsulation may be used to facilitate delivery of a nucleic acid. Microencapsulated gene delivery vehicles may be constructed from low viscosity polymer solutions that are forced to phase invert into fragmented spherical polymer particles when added to appropriate non-solvents. Methods involving microparticles are discussed in Hsu et al., J. Drug Target 7:313-323, 1999 and Capan et al., Pharm. Res. 16:509-513, 1999.

Protein transduction offers an alternative to gene therapy for the delivery of therapeutic proteins into target cells, and methods involving protein transduction are within the scope of the invention. Protein transduction is the internalization of proteins into a host cell from the external environment. The internalization process relies on a protein or peptide which is able to penetrate the cell membrane. To confer this ability on a normally non-transducing protein, the non-transducing protein can be fused to a transduction-mediating protein such as the antennapedia peptide, the HIV TAT protein transduction domain, or the herpes simplex virus VP22 protein. See Ford et al., Gene Ther. 8:1-4, 2001.

There are two major approaches to getting the nucleic acid (optionally contained in a vector) into a subject's cells; in vivo and ex vivo. For in vivo delivery the nucleic acid is injected directly into the subject, usually at the site where the nucleic acid is needed. For ex vivo treatment, the subject's cells are removed, the nucleic acid is introduced into these isolated cells and the modified cells are administered to the subject either directly or, for example, encapsulated within porous membranes which are implanted into the subject (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, viral vectors and the like. A commonly used vector for ex vivo and in vivo delivery is a viral vector as discussed above.

Host cells can be transfected or transformed with expression or cloning vectors described herein and cultured in conventional nutrient media modified as appropriate for inducing promoters, selecting transformants, or amplifying the nucleic acids encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991) and Sambrook et al.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with Agrobacterium tumefaciens is used for transformation of certain plant cells, as described by Shaw et al., Gene, 23:315 (1983) and WO 89/05859 published 29 Jun. 1989. For mammalian cells without such cell walls, the calcium phosphate precipitation method of Graham and van der Eb, Virology, 52:456-457 (1978) can be employed. General aspects of mammalian cell host system transfections have been described in U.S. Pat. No. 4,399,216. Transformations into yeast are typically carried out according to the method of Van Solingen et al., J. Bact., 130:946 (1977) and Hsiao et al., Proc. Natl. Acad. Sci. (USA), 76:3829 (1979). However, other methods for introducing DNA into cells, such as by nuclear microinjection, electroporation, bacterial protoplast fusion with intact cells, or polycations, e.g., polybrene, polyornithine, ray also be used. For various techniques for transforming mammalian cells, see Keown et al., Methods in Enzymology, 185:527-537 (1990) and Mansour et al., Nature, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as E. coli. Various E. coli strains are publicly available, such as E. coli K12 strain MM294 (ATCC 31,446); E. coli X1776 (ATCC 31,537); E. coli strain W3110 (ATCC 27,325) and K5 772 (ATCC 53,635). Other suitable prokaryotic host cells include Enterobacter, Erwinia, Klebsiella, Proteus, Salmonella, e.g., Salmonella typhimurium, Serratia, e.g., Serratia marcescans, and Shigella, as well as Bacilli such as B. subtilis and B. licheniformis (e.g., B. licheniformis 41P disclosed in DD 266,710 published 12 Apr. 1989), Pseudomonas such as P. aeruginosa, and Streptomyces. These examples are illustrative rather than limiting.

In addition to prokaryotes, eukaryotic microbes such as filamentous fungi or yeast are suitable cloning or expression hosts. Saccharomyces cerevisiae is a commonly used lower eukaryotic host microorganism. Others include Schizosaccharomyces pombe, Kluyveromyces hosts such as, e.g., K. lactis, K. fragilis, K. bulgaricus, K. wickeramii, K. waltii, K. drosophilarum, K. thermotolerans, and K. marxianus; yarrowia; Pichia pastoris; Candida; Trichoderma reesia; Neurospora crassa; Schwanniomyces such as Schwanniomyces occidentalis; and filamentous fungi such as, e.g., Neurospora, Penicillium, Tolypocladium, and Aspergillus hosts such as A. nidulans and A. niger. Methylotropic yeasts are suitable herein and include, but are not limited to, yeast capable of growth on methanol selected from the genera consisting of *Hansenula, Candida, Kloeckera, Pichia, Saccharomyces, Torulopsis,* and *Rhodotorula.* A list of specific species that are exemplary of this class of yeasts may be found in C. Anthony, The Biochemistry of Methylotrophs, 269 (1982).

Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59, 1977); baby hamster kidney cells (BHK, ATCC CCL 10); Chinese hamster ovary cells/-DHFR (CHO, Urlaub et al., Proc. Natl. Acad. Sci. USA 77:4216, 1980); mouse sertoli cells (TM4, Mather, Biol. Reprod. 23:243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68, 1982); MRC 5 cells; FS4 cells; and a human hepatoma line (Hep G2).

Host cells are transformed with the above-described Hsp90 or ZAP-70 nucleic acid expression or cloning vectors and cultured in conventional media modified as appropriate for inducing promoters, selecting transformants, or amplifying the nucleic acids encoding the desired sequences.

The Hsp90 or ZAP-70 inhibitory nucleic acids (e.g., antisense, RNAi, ribozymes, variants, coding sequences and the like) may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli.*

Examples of suitable selectable markers for mammalian cells are those that enable the identification of cells competent to take up the BDB oligopeptide-encoding nucleic acid, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216, 1980. A suitable selection gene for use in yeast is the trp1 gene present in the yeast plasmid YRp7 (Stinchcomb et al., Nature, 282:39, 1979; Kingsman et al., Gene, 7:141, 1979; Tschemper et al., Gene, 10:157, 1980). The trp1 gene provides a selection marker for a mutant strain of yeast lacking the ability to grow in tryptophan.

In another embodiment, the invention provides pharmaceutical compositions comprising an a gent identified by a method of the invention, a small molecule agent, an inhibitory nucleic acid agent, and instructions for use of the agent in the treatment of a cell proliferative disorder. For example, the methods of the invention are suitable for use in preventing dividing cells from further replication by promoting apoptosis.

The invention provides methods and compositions for treating a subject having a cell proliferative disorder such a human leukemia (e.g., chronic lymphocytic Leukemia (CLL)). The subject can be any mammal, and is preferably a human. The contacting can be in vivo or ex vivo. Methods of administering pharmaceutical compositions are known in the art and include, for example, systemic administration, topical administration, intraperitoneal administration, intra-muscular administration, as well as administration directly at the site of a tumor or cell-proliferative disorder and other routes of administration known in the art.

The pharmaceutical compositions according to the invention may be administered locally or systemically. By "therapeutically effective dose" is meant the quantity of a compound Cr agent according to the invention necessary to prevent, to cure or at least partially arrest the symptoms of the disease and its complications. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of particular disorders Various considerations are described, e.g., in Langer, Science, 249: 1527, (1990); Gilman et al. (eds.) (1990), each of which is herein incorporated by reference.

As used herein, "administering a therapeutically effective amount" includes methods of giving or applying a pharmaceutical composition of the invention to a subject that allow the composition to perform its intended therapeutic function. The therapeutically effective amounts will vary according to factors such as the degree of infection in a subject, the age, sex, and weight of the individual. Dosage regimen can be adjusted to provide the optimum therapeutic response. For example, several divided doses can be administered daily or the dose can be proportionally reduced as indicated by the exigencies of the therapeutic situation.

As used herein, a "pharmaceutically acceptable carrier" is intended to include solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the pharmaceutical composition, use thereof in the therapeutic compositions and methods of treatment is contemplated. Supplementary active compounds can also be incorporated into the compositions.

The principal pharmaceutical composition is compounded for convenient and effective administration in effective amounts with a suitable pharmaceutically acceptable carrier in an acceptable dosage unit. In the case of compositions containing supplementary active ingredients, the dosages are determined by reference to the usual dose and manner of administration of the ingredients.

Further, methods of the invention can be performed alone or in conjunction with standard medical treatments currently available for treating a cell proliferative disorder such as leukemia For example, when a tumor is being treated, it may be preferable to remove the majority of a tumor surgically or by radiation prior to introducing an agent of the invention in to the cells comprising the cell proliferative disorder.

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for a neoplastic disorder/cancer if, after receiving a therapeutic amount of a Hsp90 or ZAP-70 antagonist or Hsp90 inhibitor the subject shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues.

As used herein a cell proliferative disorder include disorders associated with an overgrowth of connective tissues, such as various fibrotic conditions, including scleroderma, arthritis and liver cirrhosis. Cell proliferative disorders include neoplastic disorders such as head and neck carcinomas. Head and neck carcinomas would include, for example, carcinoma of the mouth, esophagus, throat, larynx, thyroid gland, tongue, lips, salivary glands, nose, paranasal sinuses, nasopharynx, superior nasal vault and sinus tumors, esthesioneuroblastoma, squamous call cancer, malignant melanoma, sinonasal undifferentiated carcinoma (SNUC) or blood neoplasia. Also included are carcinoma's of the regional lymph nodes including cervical lymph nodes, prelaryngeal lymph nodes, pulmonary juxtaesophageal lymph nodes and submandibular lymph nodes (Harrison's Principles of Internal Medicine (eds., Isselbacher, et al., McGraw-Hill, Inc., 13th Edition, pp 1850-1853, 1994). Other cancer types, include, but are not limited to, lung cancer, colon-rectum cancer, breast cancer, prostate cancer, urinary tract cancer, uterine cancer lymphoma, oral cancer, pancreatic cancer, leukemia, melanoma, stomach cancer and ovarian cancer.

Methods involving conventional molecular biology techniques are described herein. Such techniques are generally known in the art and are described in detail in methodology treatises such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Various techniques using polymerase chain reaction (PCR) are described, e.g., in Innis et al., PCR Protocols: A Guide to Methods and Applications, Academic Press: San Diego, 1990. PCR-primer pairs can be derived from known sequences by known techniques such as using computer programs intended for that purpose (e.g., Primer, Version 0.5, 81991, Whitehead Institute for Biomedical Research, Cambridge, Mass.). Methods for chemical synthesis of nucleic acids are discussed, for example, in Beaucage and Carruthers, Tetra. Letts. 22:1859-1862, 1981, and Matteucci et al., J. Am. Chem. Soc. 103:3185, 1981. Chemical synthesis of nucleic acids can be performed, for example, on commercial automated oligonucleotide synthesizers. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992. Conventional methods of gene transfer and gene therapy can also be adapted for use in the invention. See, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996.

The working examples below are provided to illustrate, not limit, the invention.

EXAMPLES

Cells and Reagents

Peripheral blood mononuclear cells (PBMC) from CLL patients were obtained from the CLL Research Consortium (CRC) tissue bank. PBMC were isolated by density gradient centrifugation over Histopaque 1077. These samples had more than 95% $CD19^+/CD5^+$ cells by flow cytometry. ZAP-70 expression and $IgV_H$ gene mutational status were assessed. Cells were incubated in RPMI media at 37° C. with 5% $CO_2$. The MCF7 breast cancer cells were obtained from the American Type Culture Collection (ATCC) (Manassas, Va.). In some experiments the cells were treated with 2-Fluoro-Ara-A, 17-DMAG (InvivoGen, San Diego, Calif.), 17-AAG, or EC116 (17-AAG analogue) (Conforma Therapeutics Inc. San Diego, Calif.). The biotin-GM probe was prepared by displacing the 17-methoxy of GM with a biotinyl-linked amine. Cell samples were incubated also in media with DMSO (1%) as a control.

Antibodies used were: Hsp90 (Stressgen, SPA-835; recognizes Hsp90α and Hsp90β and immunoprecipitates free and complexed Hsp90), Hsp90* (Stressgen, SPA-830; recognizes Hsp90α and Hsp90β and immunoprecipitates uncomplexed Hsp90; Stressgen Biotechnologies Corporation, Victoria, B.C., Canada), p 23 (804-023-R100; Alexis Biochemicals. San Diego, Calif.). Hop (a gift from D. Toft), ZAP-70 nonconjugated and Alexa 488 (Caltag Laboratories. Burlingame, Calif.), $p72^{Syk}$ (clone 4D10.1. Upstate Biotechnology, Lake Placid, N.Y.), 4G10 (Upstate Biotechnology, Lake Placid, N.Y.). Hsp70 (Stressgen Biotechnologies Corporation, Victoria, B.C., Canada), CD3-PE (BDPharmingen. San Diego, Calif.), β actin (clone AC-15, Sigma Immunochemicals, St Louis, Mo.), anti-PARP-1 (clone C2-10, BD Pharmingen, La Jolla, Calif.), IkB-α, and IKK-α (BDPharmingen)

Hsp90 Binding Assays

Purified native Hsp90 protein (Stressgen Biotechnologies Corporation, Victoria, B.C., Canada) or cell lysates from cells that had been gently lysed by manual douncing in a Potter-Elvejem homogenizer in lysis buffer (20 mM HEPES, pH 7.3, 1 mM EDTA, 5 mM $MgCl_2$, 100 mM KCl) were incubated with or without 17-AAG for 30 min at 4° C., and then incubated with biotin-GM linked to BioMag streptavidin magnetic beads (Qiagen. Valencia, Calif.) for 1 h at 4° C. Tubes were placed on a magnetic rack, and the unbound supernatant removed. The magnetic beads were washed in lysis buffer and heated for 5 min at 95° C. in SDS-PAGE sample buffer. Samples were analyzed on SDS protein gels, and immunoblots performed using the indicated antibodies. The band intensities in the immunoblots were assessed using the Biorad Fluor-S MultiImager, and the percentage inhibition of binding of Hsp90 to the biotin-GM calculated. The reported $IC_{50}$ is the concentration of 17-AAG required to cause half-maximal inhibition of binding.

Immunoblot and Co-Immunoprecipitation

Lysates were prepared as described above. Protein-A Sepharose beads (Zymed Laboratories Inc South San Francisco, Calif.) were pre-blocked with 5% BSA. The cell lysates were pre-cleared by incubating with 50 µl of protein-A Sepharose beads (50% slurry). To 100 µl of the pre-cleared cell lysate, either no antibody or antibodies to Hsp90, ZAP-70, p23, Hop, or p72$^{Syk}$ were added, and incubated by rotating for 1 h at 4° C. Fifty µl of pre-cleared beads (50% slurry) were then added and incubated by rotating for 1 h at 4° C. Bound beads were centrifuged at 3,000×g and unbound samples were collected.

Beads were washed thrice in lysis buffer and then once with 5 µM Tris, pH 6.8. We added SDS-sample buffer and then incubated the samples for 5 min at 95° C. Bound and unbound samples were analyzed by SDS-PAGE and immunoblot analyses using the indicated antibodies.

Protein lysates for immunoblot studies were prepared using RIPA buffer with protease inhibitors (10 µg/ml aprotinin, 10 µg/ml leupeptin, 10 µg/ml pepstatin and 1 mM phenylmethylsulfonyl fluoride), and in some cases phosphatase inhibitors (1 mM Na-Vanadate and 10 mM β-Glycerophosphate). Membranes were probed with antibodies as indicated. Detection was accomplished by chemiluminescence using horseradish peroxidase (HRP) conjugated antibodies followed by development with ECL Plus (Amersham-Biosciences Piscataway, N.J.) and autoradiography with Super RX film (Fuji, Tokyo, Japan)

Flow Cytometry and Apoptosis Detection

Fluorochrome-conjugated monoclonal antibodies were used for flow cytometry. The samples were processed using a FACScalibur (Becton-Dickinson B D, Franklin Lakes, N.J.) and the data were analyzed using Flo-Jo 3.6 software (Stanford University-Tree Star Inc. San Francisco, Calif.). Apoptotic and viable cells were discriminated via flow cytometry with 3,3' dihexyloxacarbocyanine iodide ($DiOC_6$) (Molecular Probes, Eugene, Oreg.) and propidium iodide (Sigma, St. Louis, Mo.). Using this method viable cells exclude PI and stain brightly positive for $DiOC_6$.

Adenovirus Transduction of CLL Cells cDNA of ZAP-70 extracted from normal T cells was cloned into the CMV promoter and polyadenylation signal of pcDNA3. This construct was then subcloned into the shuttle vector MCS(SK)pXCX2. This shuttle vector was cotransfected with pJM17 into 293 cells using the calcium phosphate method.

Isolated adenovirus plaques were harvested and used to infect 293 cells. High titer adenovirus preparations were obtained. CLL cells were infected with either Ad-ZAP-70 or a control adenovirus vector (Ad-LacZ) for 48 hours at 37° C. using a multiplicity of infection (MOI) of 1000.

Hsp90 inhibitors induce apoptosis in CLL cells that express adverse prognostic markers. Primary leukemia cells (n=25) were treated with 17-AAG and examined for drug induced apoptosis at 48 hours (Table 1). Leukemia cells that used unmutated IgV$_H$ genes were significantly move sensitive to 17-AAG than CLL cells that expressed mutated IgV$_H$ genes (FIG. 1A) (P≤0.05). Furthermore, there was a significant association between the level of apoptosis induced at 48 hours by 17-AAG and the level of ZAP-70 expressed by the each of the leukemia-cell samples (r2=0.9022) (FIG. 1B).

TABLE 1

Characteristics of patient samples used in this study

| Patient no. | Sex/age, y | Rai/Binetcount, staging | Lymphocyte × $10^9$/L | ZAP-70 expression, % | IgV$_H$ homology | 17-AAG-induced apoptosis, % | % Active Hsp90 | Number of previous treatments |
|---|---|---|---|---|---|---|---|---|
| 1 | M/64 | 2/A | 419 | 0.4 | Mutated | 3.9 | 27.7 | 2 |
| 2 | M/58 | 2/A | 66 | 0.4 | Mutated | 4.5 | 8.8 | 0 |
| 3 | M/43 | 2/A | 62 | 0.6 | Mutated | 1.2 | 12 | 0 |
| 4 | F/67 | 2/A | 18 | 0.8 | Unmutated | 4.7 | 27.5 | 0 |
| 5 | M/50 | 2/B | 193 | 1.5 | Mutated | 11.5 | 0 | 2 |
| 6 | M/75 | 2/A | 25 | 2.0 | Mutated | 12.3 | 0 | 0 |
| 7 | F/65 | 2/A | 74 | 6.3 | Mutated | 14.9 | 10.4 | 2 |
| 8 | F/62 | 2/A | 109 | 6.8 | Mutated | 3.7 | ND | 0 |
| 9 | F/63 | 1/A | 85 | 9.4 | Unmutated | 0.5 | ND | 1 |
| 10 | F/59 | 1/A | 112 | 10.6 | Mutated | 12.6 | ND | 0 |
| 11 | F/60 | 3/C | 96 | 12.3 | Mutated | 3.4 | 4.1 | 5 |
| 12 | F/55 | 2/B | 240 | 18.8 | Unmutated | 22.4 | ND | 2 |
| 13 | M/59 | 3/C | 55 | 20.3 | Mutated | 55.4 | ND | 1 |
| 14 | M/77 | 2/B | 101 | 29.1 | Unmutated | 33.9 | 100 | 0 |
| 15 | F/67 | 2/A | 560 | 29.1 | Unmutated | 37.9 | ND | 2 |
| 16 | M/67 | 2/A | 60 | 43.2 | Unmutated | 35.4 | 100 | 2 |
| 17 | F/60 | 2/A | 68 | 54.6 | Unmutated | 41.3 | 99 | 2 |
| 18 | F/48 | 1/A | 9 | 59.0 | Unmutated | 57.9 | 99 | 1 |
| 19 | M/67 | 4/C | 60 | 67.1 | Unmutated | 57.7 | ND | 2 |
| 20 | F/61 | 1/A | 33 | 81.9 | Unmutated | 67.4 | 99 | 0 |
| 21 | M/50 | 2/A | 89 | 85.5 | Unmutated | 69.4 | 100 | 1 |
| 22 | F/49 | 4/C | 57 | 87.1 | Unmutated | 66.8 | 100 | 4 |
| 23 | F/75 | 2/A | 61 | 90.5 | Unmutated | 78.8 | ND | 0 |
| 24 | M/70 | 2/A | 93 | 91.1 | Unmutated | 79.9 | ND | 0 |
| 25 | F/54 | 1/A | 32 | 91.9 | Unmutated | 74.4 | 99 | 0 |

17-DMAG, another Hsp90 inhibitor, induced a similar pro-apoptotic activity in CLL cells. However, a synthetic analogue of 17-AAG lacking the capacity to inhibit Hsp90 (EC116) did not induce significant apoptosis (FIGS. 1C, D).

Figure 2:
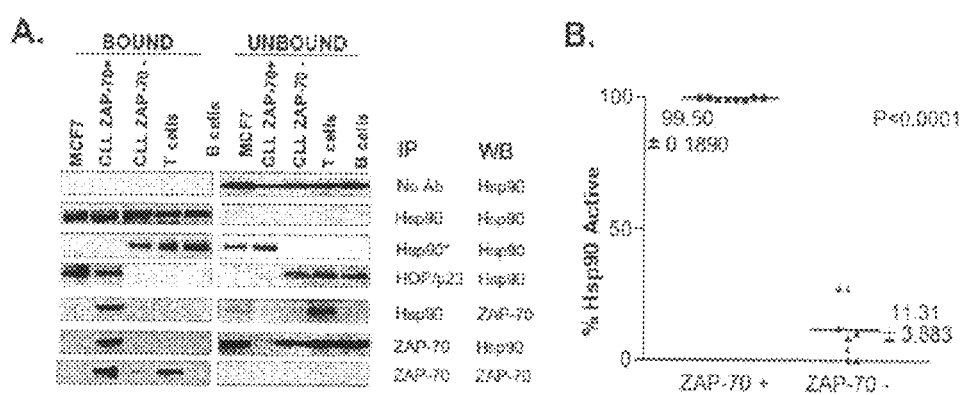
FIGS. 2A-B show that ZAP-70 physically associates with activated Hsp90 in CLL cells. (A) Protein lysates from different cell types including ZAP-70$^+$ and negative CLL cells, normal T and B cells and the breast cancer cell line MCF7 were immunoprecipitated (IP) with the indicated antibodies including Hsp90*, which is an antibody that recognizes the uncomplexed form of Hsp90. The bound and unbound IP products were probed by immunoblot using the antibodies indicated in the WB column. (B) IP was used to assess the level of expression of complexed (activated) and uncomplexed (non-activated) Hsp90 in different CLL samples (8 ZAP-70$^+$ CLL and 8 ZAP-70-negative CLL). The figure shows the percentage of activated Hsp90 for each sample. This percentage was calculated after analyzing the digitalized composite ratio of immunoblot signal for Hsp90 uncomplexed and total Hsp90 using the following formula: % $Hsp90_{active}=1-(Hsp90*/Hsp90_{total})\times100$.

ZAP-70 physically associates with activated Hsp90 in CLL cells. Protein lysates from primary leukemia cells were immunoprecipitated using different specific monoclonal antibodies, as shown in (FIG. 2A). CLL cells were defined as ZAP-70+ if >20% of the stained cells were positive by flow cytometry. Controls included purified human B and T cells from normal subjects and MCF-7, a breast cancer cell line that expresses large amounts of activated Hsp90. All samples expressed similar levels of Hsp90. ZAP-70+ CLL and MCF-7 cells expressed Hsp90 that was complexed with the co-chaperones Hop and p23.

Immunoprecipitation with an antibody that recognizes the uncomplexed form of Hsp90 (Hsp90*), however, revealed that ZAP-70-negative CLL samples, as well as T and B cells of healthy donors, expressed the uncompleted (non-active) form of Hsp90. These results were consistently reproduced in larger numbers of CLL samples (n=16) (FIG. 2B). Interestingly, the ZAP-70 expressed in CLL cells, but not in normal T cells, communoprecipitated with Hsp90, suggesting that this tyrosine kinase is a conditional Hsp90 client protein as its client status varies depending on the cell in which it is expressed.

Figure 3:
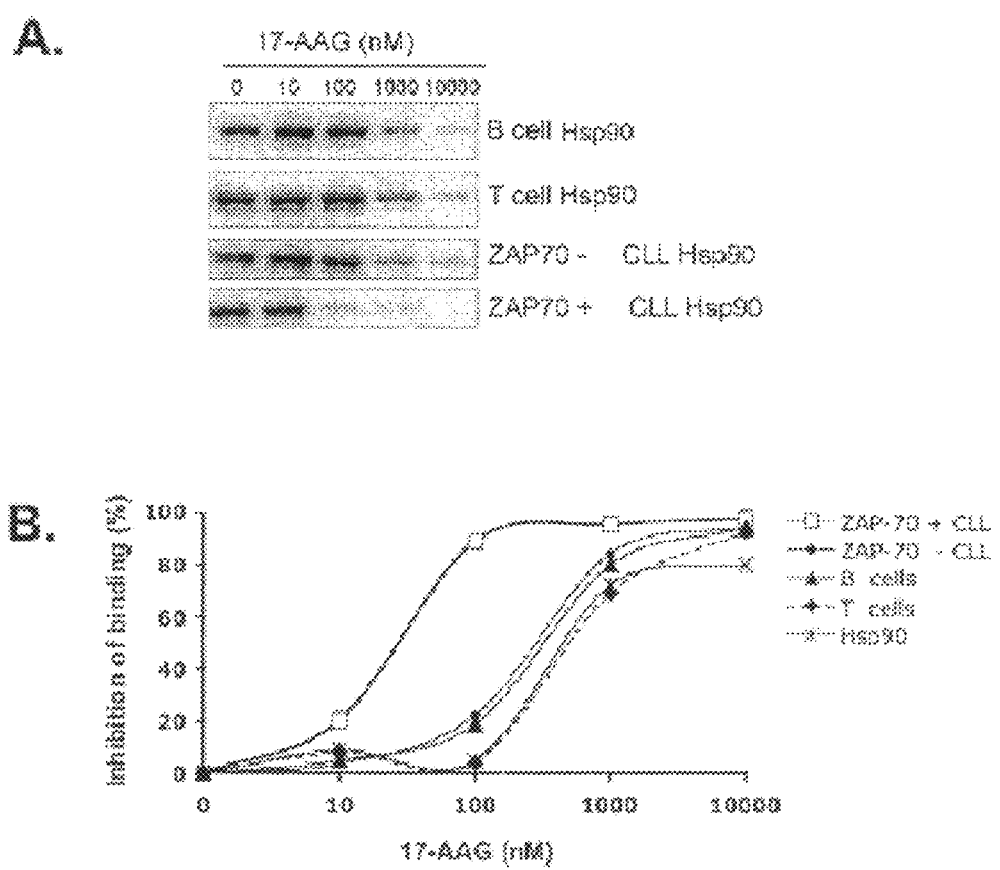
FIGS. 3A-B show Hsp90 expressed in ZAP-70+ CLL has increased binding affinity for 17-AAG. (A) Protein lysates from different samples were evaluated for their binding affinity to Hsp90 inhibitors in a competitive binding assays using a biotinylated geldanamycin (biotin-GM) probe and increasing concentrations of 17-AAG. (B) Hsp90 derived from ZAP-70+ CLL cells showed a higher binding affinity for 17-AAG with an $IC_{50}$ of 31 nM (SEM±2), whereas Hsp90 from ZAP-70-negative CLL cells, normal B and T cells had an $IC_{50}\geq300$ nM. Purified recombinant Hsp90 had an $IC_{50}$ of 600 nM. This experiment was reproduced three times.

Competitive binding assays were performed using a biotinylated GM (biotin-GM) probe to investigate whether the differential expression of active Hsp90 in CLL samples correlated with their binding affinity to 17-AAG (FIGS. 3A, B). Addition of 17-AAG to cell lysates inhibited the binding of Hsp90 to biotin-GM in a dose-dependent fashion, with ZAP-70+ CLL-cell lysates experiencing an $IC_{50}$ of 31 nM (n=3; SEM±2). In contrast, the $IC_{50}$ was ≥300 nM for lysates from ZAP-70-negative CLL cells or normal T or B cells. Purified native Hsp90 protein binding was inhibited with an $IC_{50}$ of 600 nM (FIGS. 3A, B).

Figure 4:
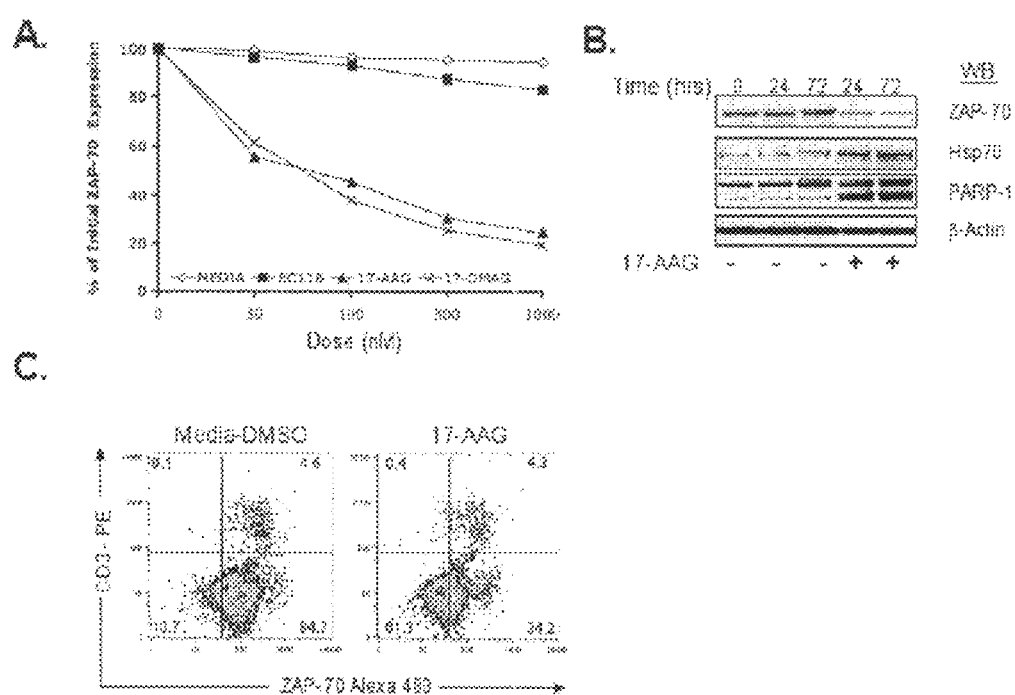
FIGS. 4A-C shows that inhibition of Hsp90 induces degradation of ZAP-70 in CLL cells but not in T cells. (A) ZAP-70+ CLL cells were treated in vitro with increasing concentrations of 17-AAG (▲), 17-DMAG (×) and the analogue EC116 (■) for 48 hours. Cells incubated in media with DMSO 1% final concentration were used as a control (◇). ZAP-70 expression was evaluated by intracellular staining. (B) ZAP-70 expression in CLL cells after treatment with 17-AAG (100 nM) was evaluated by immunoblot at different time points. In addition, immunoblots were probed with anti-Hsp70 and anti-poly ADP-ribose polymerase (PARP-1) monoclonal antibodies. β-actin was used as a protein loading control. Apoptosis after treatment with 17-AAG was 30% and 50% at 24 and 72 hours respectively. (C) Peripheral blood mononuclear cells from ZAP-70+ patients were treated for 48 hours with 17-AAG (300 nM). The cells were stained with specific antibodies and analyze by flow cytometry. The panel shows a density plot of cells labeled with anti-CD3 and anti-ZAP-70 antibodies. In each quadrant the percentage of cells is shown. The ZAP-70 mean florescence intensity (MFI) prior to treatment with 17-AAG in CLL cells was 110 and in T cells was 210. The post-treatment MFI value for ZAP-70 was 25 for CLL cells and 190 for T cells.

Inhibition of Hsp90 induces degradation of ZAP-70 in CLL cells but not in T cells. The expression levels of ZAP-70 in leukemia cells treated in vitro with 17-AAG, 17-DMAG and a control synthetic analogue (EC116) was monitored. After 24 hours, 17-AAG and 17-DMAG caused a specific dose-dependent reduction of leukemia-cell ZAP-70 expression ($IC_{50}$=60 nM) This effect was not observed in the samples treated with EC116 or media containing DMSO (FIGS. 4A, B). Down-regulation of ZAP-70 after incubation with Hsp90 inhibitors correlated with cleavage of PARP-1, indicating leukemia-cell apoptosis. It also correlated with the upregulation of Hsp70, a chaperone protein that is induced by inhibition of active Hsp90 (FIG. 4B). Of note, treatment with 17-AAG did not affect ZAP-70 expression levels in T cells from CLL patients or healthy donors, even at high concentrations (≥300 nM) (FIG. 4C).

Figure 5:
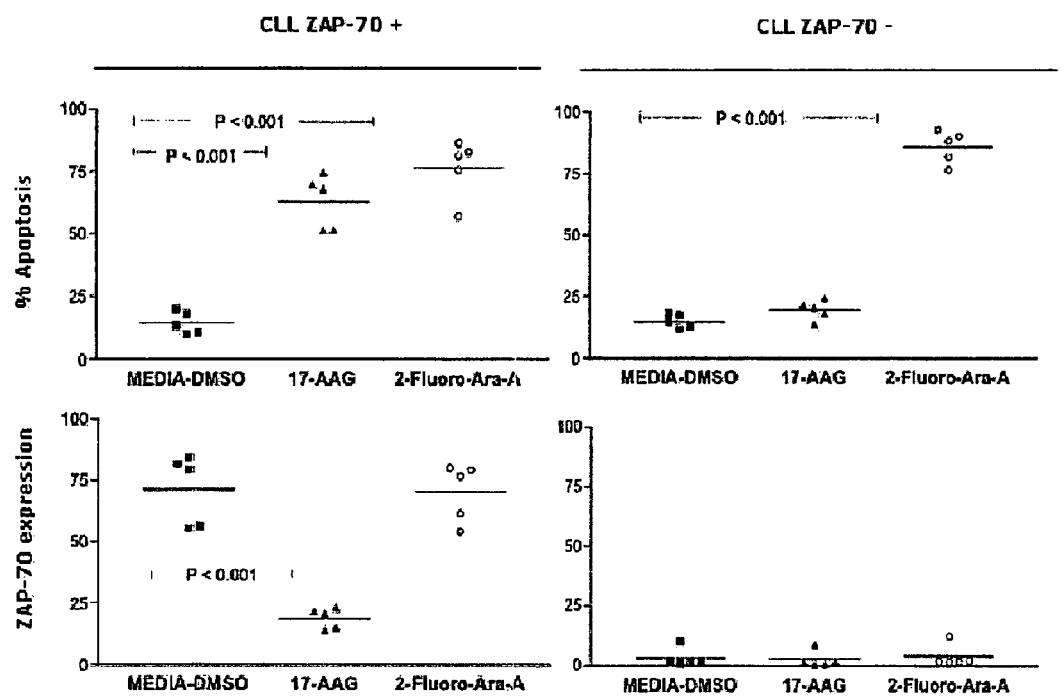
FIG. 5 shows that degradation of ZAP-70 mediated by Hsp90 inhibitors is specific and is not induced by cytotoxic chemotherapy in vitro. ZAP-70+ and ZAP-70-negative CLL cells (n=10), were treated with 17-AAG (100 nM) and 2-Fluoro-Ara-A (2.5 µM) for 48 hours. Flow cytometry was used to assess apoptosis (upper panels) and ZAP-70 expression (lower panels) on each sample. Control samples were incubated with Media-DMSO as indicated. Error bars indicate the mean value for each group. P values were calculated using a One-way ANOVA with Bonferroni post-test analysis.

In addition, treatment of CLL cells with Fludara (2-Fluoro-Ara-A) did not induced down-regulation of ZAP-70 despite promoting apoptosis in leukemia cells. This suggests that down-regulation of ZAP-70 after treatment with Hsp90 inhibitors is specific and not due to apoptosis induced by an anti-leukemia agent per se (FIG. 5).

Figure 6:
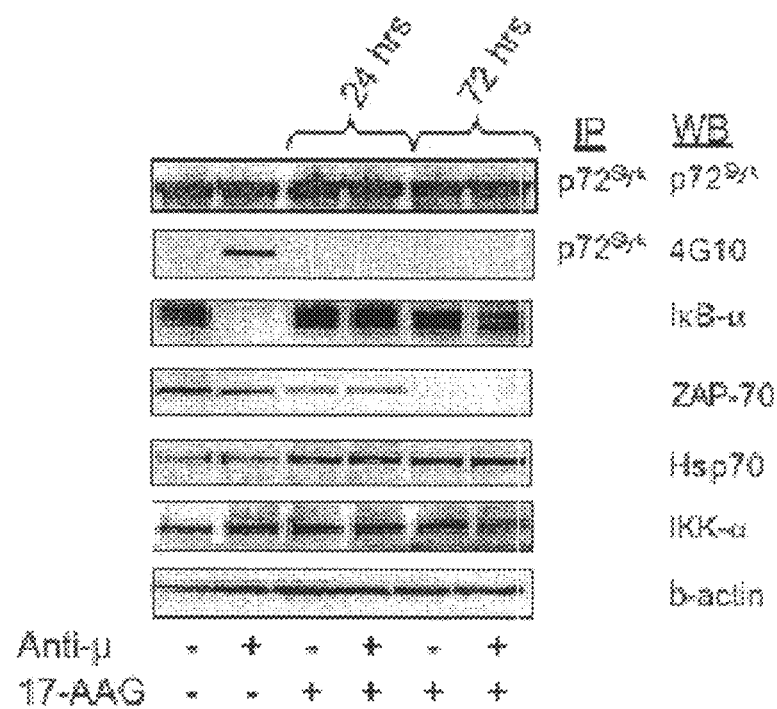
FIG. 6 are gels showing that inhibition of Hsp90 impairs B-cell receptor (BCR) signaling in ZAP-70+ CLL cells. ZAP-70+ CLL cells were pre-incubated with 17-AAG for 24 and 72 hours and then treated for 10 minutes with F(ab')2 anti-µ antibodies to induce cellular activation. Pxotein lysates were immunoprecipitated (IP) with specific anti-$p72^{Syk}$ antibody and assessed by western blot (WB) for tyrosine phosphorylation using 4G10 antibody and $p72^{Syk}$ expression. Protein lysates from the same samples were evaluated by western blot using the indicated antibodies. Activation of NF-κB was assessed by degradation of IκB-α. These results were reproduced more than 3 times.

Inhibition of Hsp90 blocks B-cell receptor (BCR) signaling in ZAP-70+ CLL cells. ZAP-70+ CLL cells were treated with 17-AAG and their capacity to respond to ligation of the BCR with F(ab')2 anti-μ monoclonal antibody was monitored. 17-AAG did not alter the level of $p72^{Syk}$, which was detected in all samples. Stimulation of control-treated samples with anti-μ induced both phosphorylation of $p72^{Syk}$ and activation of NF-κB, as assessed by degradation of IκB-α (FIG. 6). However, prior treatment with 17-AAG for ≥24 hours rendered such leukemia cells inert to stimulation with anti-μ antibody.

Figure 7:
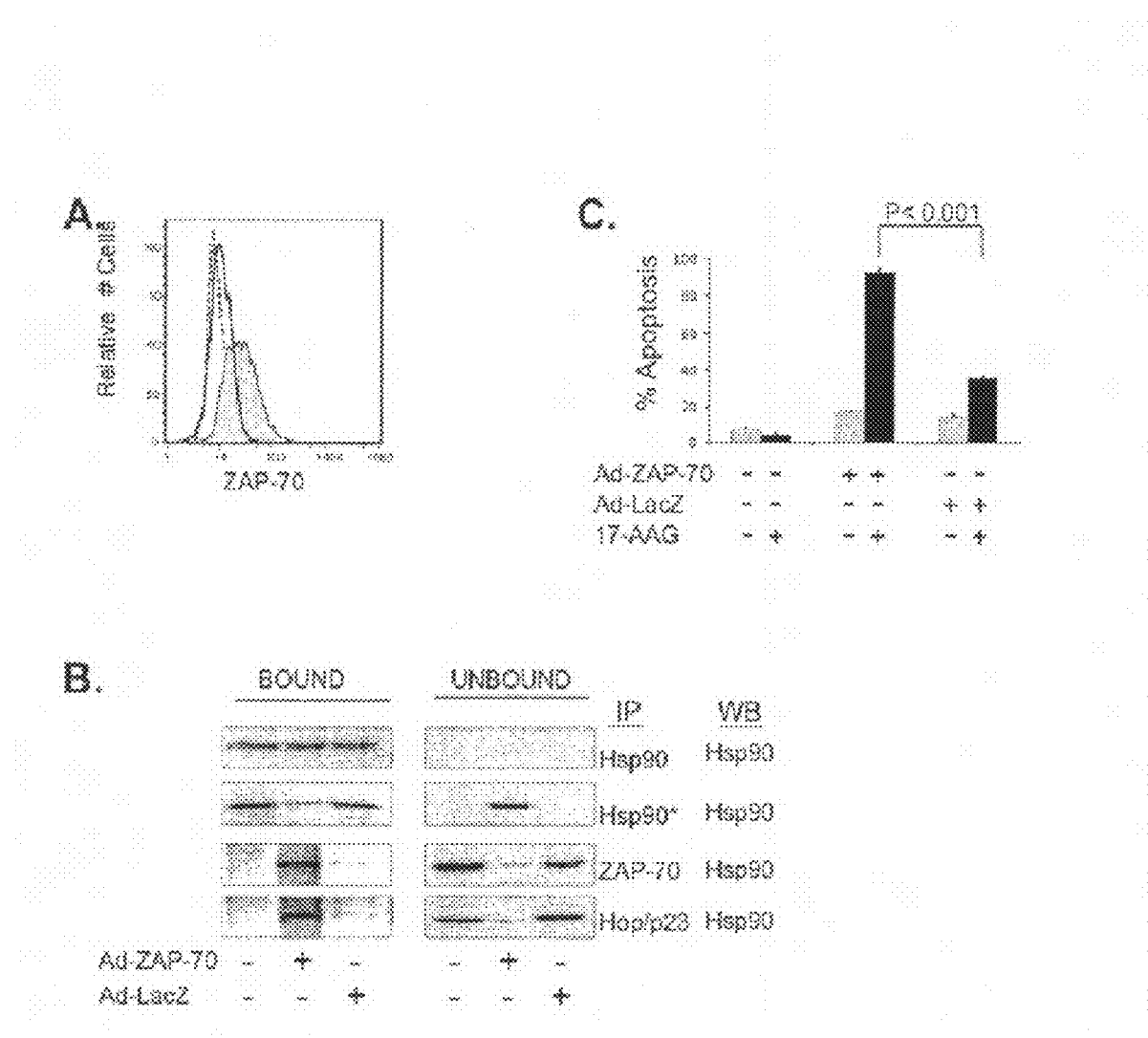
FIGS. 7A-C shows that transduction of CLL cells to express ZAP-70 activates Hsp90 and induces sensitivity to 17-AAG mediated apoptosis. (A) ZAP-70-negative leukemia cells were transduced with adenovirus expressing ZAP-70 (Ad-ZAP-70—solid histogram) and β-galactosidase (Ad-LacZ—bold line histogram). Cells were kept in media as a control (dashed line histogram). After 48 hours in culture Ad-ZAP-70 but not Ad-LacZ transduced cells expressed the ZAP-70 transgene (46% expression with a mean fluorescence intensity ratio (MFIR) of 2.8). (B) ZAP-70-negative CLL cells were transduced with adenovirus and after 48 hours they were harvested and lysed. Immunoprecipitations (IP) and immunoblots were performed with the antibodies indicated. The bound fractions represent the immunoprecipitated proteins and the unbound samples represent the soluble protein lysate after IP. (C) After 48 hours of transduction with adenovirus the leukemia cells were treated in vitro with 17-AAG (100 nM) for additional 48 hours and then assessed for apoptosis by flow cytometry using $DiOC_6$ and PI. After treatment with 17-AAG, CLL cells transduced with Ad-ZAP-70 had a significantly higher level of apoptosis compared with non-transduced or Ad-LacZ transduced cells P≤0.001.

Transduction of CLL cells to express ZAP-70 activates Hsp90 and induces sensitivity to 17-AAG mediated apoptosis. ZAP-70-negative CLL cells were transduced with an adenovirus vector encoding ZAP-70 (Ad-ZAP-70) or β-galactosidase (Ad-LacZ) as a control. After 48 hours, Ad-ZAP-70-transduced CLL cells expressed ZAP-70 at levels that were comparable to that of ZAP-70+ CLL cells (FIG. 7A). Transduction of CLL cells with Ad-ZAP-70, but not Ad-LacZ, induced formation of Hop and p23 multi-chaperone complexes, indicating a change in the conformation of Hsp90 from the latent state to the activated complexed form (FIG. 7B). In addition, the de novo expression of ZAP-70 sensitized the cells to 17-AAG, which now could induce apoptosis in ZAP-70 transduced CLL cells even at low drug concentrations (FIG. 7C).

The invention demonstrates that ZAP-70 is an Hsp90 client protein in CLL cells but not in T cells and that ZAP-70 degradation via inhibition of Hsp90 leads to impaired signaling after BCR ligation and leukemia cell apoptosis.

CLL cells from different patients vary in their susceptibility to apoptosis induced by treatment with Hsp90 inhibitors. The basis for this includes a statistically significant correlation between the relative sensitivity to 17-AAG and expression of unmutated $IgV_H$ genes and ZAP-70. Moreover, there was a significant association between the level of apoptosis induced by 17-ARG and the level of ZAP-70 expression in the leukemia-cell samples.

Consistent with this ZAP-70+ CLL cells expressed Hsp90 in multichaperone complexes with high binding affinity for 17-AAG. Conversely, ZAP-70-negative CLL cells as well as normal T and B-lymphocytes expressed the inactive, uncomplexed form of Hsp90. This is consistent with data showing that the molecular basis for the selective antitumor activity of 17-AAG and other ansamycins is related to the presence of an increased binding affinity to these compounds in tumor tissues compared with normal cells. The increased affinity appears to be due to cochaperone-induced changes in the ATP binding site of Hsp90, because tumor Hsp90 is present entirely in multi-chaperone complexes with high ATPase activity, whereas Hsp90 from normal tissues is in a latent, apparently uncomplexed state. In addition, the degree of Hsp90 activation correlated with expression of certain client kinases associated with poor prognosis, most notably HER-2 in breast cancer. The invention demonstrates that Hsp90 activation and sensitivity to 17-AAG in early-stage CLL cells correlate with poor prognostic factors such as unmutated $IgV_H$ genes and expression of ZAP-70 kinase.

The invention demonstrates that ZAP-70 associates with activated Hsp90 in CLL cells and that treatment with Hsp90 inhibitors, such as 17-AAG or 17-DMAG, induced specific degradation of this kinase. Consistent with this, degradation of p72Syk in 17-AAG-treated CLL cells was not observed, despite the high-degree of similarity of this protein kinase to ZAP-70. Also, treatment with 2-Fluoro-Ara-A did not induced changes in ZAP-70 expression despite of inducing apoptosis in CLL cells. This indicates that down-regulation of ZAP-70 mediated by Hsp90 inhibitors is a specific effect that is not due to proteolysis induced by apoptosis per se.

The data indicate that ZAP-70 is itself an Hsp90 client protein susceptible to specific degradation induced by Hsp90 inhibitors. Interestingly, the requirement for Hsp90 chaperoning support by ZAP-70 was limited to CLL cells and was not observed in T cells where this kinase is normally expressed 17. In this particular sense, ZAP-70 is unique among identified Hsp90 clients as its chaperone dependency is conditional upon the type of cell in which it is expressed.

The transduction experiments performed in ZAP-70-negative CLL cells employed a T-cell-derived ZAP-70 construct, suggests that sequence or splicing variation of the ZAP-70 gene in CLL cells or T cells are not responsible for these discrepancies. Post-translational modifications (e.g. phosphorylation, SUMOylation, or acetylation) or changes in tertiary structure required to accommodate different substrates may underlie the differential chaperoning support required by ZAP-70 in CLL cells versus T cells.

It is conceivable that the expression of non-mutated oncogenic kinases or proteins in non-physiological cell types or intracellular compartments may render them chaperone-dependent. Although we are unaware of other examples of proteins acquiring Hsp90 dependence due to inappropriate expression in a different mammalian cell, there are parallels in other systems. Viruses must translate their proteins in the foreign environment of the host cell, and several essential proteins of such human pathogens are Hsp90 clients, including the HBV reverse transcriptase and HCV protease. Similarly, the bovine serum albumin protein attains client status when it is inappropriately expressed in the HeLa cell cytosol, presumably because it adopts an aberrant conformation.

Activated Hsp90, 17-AAG-mediated ZAP-70 degradation or apoptosis in normal T cells or T cells derived from patients with CLL was not observed, even when higher concentrations of 17-AAG were used. In addition, Hsp90 from T cells had a 10-fold lower binding affinity for 17-AAG than did Hsp90 from ZAP-70$^+$ CLL cells. As such, 17-AAG and its derivatives may selectively target CLL cells at concentrations that do not affect T cells.

Treatment of ZAP-70$^+$ CLL cells with 17-AAG also resulted in loss of BCRsignaling. Expression of ZAP-70 in CLL allows for more effective IgM-signaling in CLL cells, a feature that could contribute to the relatively aggressive clinical behavior associated with CLL cells that express unmutated IgV$_H$ genes. This enhanced signaling is associated with higher levels of phosphorylated p72$^{Syk}$, BLNK, and phospholipase-Cγ, and greater Ca$^{2+}$ flux. Therefore, the invention further supports the emerging physiological role of ZAP-70 in CLL cells. The signaling events after BCR ligation might not be specifically due to inhibition of ZAP-70, as other kinases that participate in BCR signaling also may be influenced by Hsp90 inhibition. Nevertheless, 17-AAG did not induce degradation of p72$^{Syk}$ or IKK-α, suggesting that the loss of BCR-signaling most likely is due to degradation of ZAP-70 resulting from inhibition of Hsp90.

ZAP-70$^+$ CLL cells underwent apoptosis upon treatment with low concentrations of 17-AAG or 17-DMAG. This effect was time- and dose-dependent and correlated closely with the level of ZAP-70 expression. Conceivably, other proteins, including some that support leukemia-cell survival, are also degraded upon inhibition of Hsp90, thereby contributing to the effects seen in treated CLL cells. Indeed, some proteins identified as Hsp90 client proteins are known survival-signaling kinases, such as IGF-1R, Akt, Raf-1, and IKK. However, transduction of ZAP-70-negative CLL cells with an adenovirus encoding ZAP-70, but not with a control adenovirus vector, activated Hsp90 and specifically rendered the leukemia cells sensitive to apoptosis induced by 17-AAG. This indicates that the expression of wild-type ZAP-70 in CLL cells was sufficient to induce activation of Hsp90. The invention further demonstrates that ZAP-70$^+$ CLL cells are dependent on ZAP-70 for their survival and that degradation of this kinase, as observed after treatment with Hsp90 inhibitors, effectively impairs not only BCR-signaling, but also cell survival.

The invention provides differences in clinical prognosis and cancer progression in CLL linked to the activity of Hsp90. Inappropriate ZAP-70 expression in malignant cells of the B-lineage increases their malignant potential, indicating that ZAP-70 may represent an adaptive change in the somatic evolution of CLL in vivo. Provocative recent findings indicate that Hsp90 may play a buffering role in Darwinian evolution rescuing potentially misfolded mutant or aberrantly-expressed proteins such that they do not become lethal to the cell. Activation of Hsp90 protects aggressive CLL cells by stabilizing ZAP-70, thus allowing this kinase to support tumor-cell survival and/or proliferation. In addition, ZAP-70 expression in CLL cells confers heightened sensitivity to 17-AAG or 17-DMAG, indicating that Hsp90 inhibitors have substantial therapeutic activity, particularly in patients with aggressive, ZAP-70-positive disease.

A number of embodiments have been described. Nevertheless, it will be understood that various modifications may be made without departing from the spirit and scope of the description. Accordingly, other embodiments are within the scope of the following claims.

What is claimed is:

1. A method of detecting chronic lymphocytic leukemia (CLL) in a subject, comprising determining in a biological sample from the subject (i) an Hsp90-ZAP-70 complex and/or (ii) an amount of activated Hsp90 in a cell that expresses ZAP-70 in the sample, wherein if (i) and/or (ii) is elevated compared to a control, the amount is indicative of chronic lymphocytic leukemia in the subject.

2. The method of claim 1, wherein the presence of the Hsp90-ZAP-70 complex is determined by immunoprecipitation assays.

3. The method of claim 1, wherein the biological sample is obtained from the subject prior to administration of a treatment to the subject and the Hsp90-ZAP-70 complex is determined in the sample.

4. The method of claim 1, wherein the biological sample is obtained from the subject after administration of a treatment to the subject and the Hsp90-ZAP-70 complex is determined in the sample.

5. The method of claim 1, comprising reacting at least one Hsp90-ZAP-70 complex contained in the biological sample from the subject with a reagent comprising at least one antibody that interacts with the Hsp90-ZAP-70 complex or with each of Hsp90 and ZAP-70 such that the complex is labeled and detecting the complex.

6. The method of claim 3, wherein the sample comprises a neoplastic cell.

7. The method of claim 1, wherein the complex is detected by Western blot assay.

8. The method of claim 1, wherein the complex is detected by ELISA.

9. The method of claim 1, wherein the complex is detected by immunocytochemistry.

10. The method of claim 1, wherein the complex is detected by flow cytometry.

11. The method of claim 1, wherein the complex is detected by relative mobility (Mr) shift in a gel.

12. The method of claim 5, wherein the at least one antibody is at least one monoclonal antibody.

13. The method of claim 1, further comprising determining the expression of one or more additional polynucleotides or polypeptides associated with CLL.

14. The method of claim 1, wherein the subject is a mammal.

15. The method of claim 14, wherein the mammal is a human.

* * * * *